United States Patent
Rabuka et al.

(10) Patent No.: US 11,970,546 B2
(45) Date of Patent: Apr. 30, 2024

(54) ANTIBODY SPECIFIC FOR MUCIN-1 AND METHODS OF USE THEREOF

(71) Applicant: R.P. Scherer Technologies, LLC, Carson City, NV (US)

(72) Inventors: David Rabuka, Kensington, CA (US); Penelope M. Drake, Castro Valley, CA (US); Yun Cheol Kim, Walnut Creek, CA (US); Robyn M. Barfield, Emeryville, CA (US); Maxine Bauzon, Hercules, CA (US); Ayodele Ogunkoya, Emeryville, CA (US)

(73) Assignee: R.P. SCHERER TECHNOLOGIES, LLC, Carson City, NV (US)

( * ) Notice: Subject to any disclaimer, the term of this patent is extended or adjusted under 35 U.S.C. 154(b) by 315 days.

(21) Appl. No.: 17/389,723

(22) Filed: Jul. 30, 2021

(65) Prior Publication Data

US 2022/0033514 A1 Feb. 3, 2022

Related U.S. Application Data

(60) Provisional application No. 63/059,497, filed on Jul. 31, 2020.

(51) Int. Cl.
| | | |
|---|---|---|
| *C07K 16/30* | (2006.01) | |
| *A61K 39/00* | (2006.01) | |
| *A61K 47/69* | (2017.01) | |
| *A61P 35/00* | (2006.01) | |

(52) U.S. Cl.
CPC ...... *C07K 16/3076* (2013.01); *A61K 47/6911* (2017.08); *A61K 2039/505* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2004/0197328 A1* | 10/2004 | Young | C07K 16/00 424/155.1 |
| 2008/0286269 A1 | 11/2008 | Violette et al. | |
| 2016/0287720 A1 | 10/2016 | Liu et al. | |
| 2020/0239594 A1 | 7/2020 | Bamdad et al. | |

OTHER PUBLICATIONS

Almagro & Fransson, (Frontiers in Bioscience 2008; 13:1619-33) (Year: 2008).*
Gura (Science, 1997, 278:1041-1042) (Year: 1997).*
Kaiser (Science, 2006, 313: 1370) (Year: 2006).*
Chames et al (British J. of Pharmacology, 2009, 157, 220-233) (Year: 2009).*
Sørensen et al; (2006) "Chemoenzymatically synthesized multimeric Tn/STn MUC1 glycopeptides elicit cancer-specific anti-MUC1 antibody responses and override tolerance," Glycobiology, 16(2): 96-107.
Naito et al; (2017) "Generation of Novel Anti-MUC1 Monoclonal Antibodies with Designed Carbohydrate Specificities Using MUC1 Glycopeptide Library," ACS OMEGA, 2, 7493-7505.

* cited by examiner

*Primary Examiner* — Peter J Reddig
(74) *Attorney, Agent, or Firm* — KNOBBE, MARTENS, OLSON & BEAR LLP

(57) ABSTRACT

The present disclosure provides antibodies specific for Mucin 1. Nucleic acids that encode one or both of the variable chains of an antibody of the present disclosure are also provided, as are cells that include such nucleic acids. Also provided are compositions that include the antibodies of the present disclosure, including in some instances, pharmaceutical compositions. Methods of making and using the antibodies of the present disclosure are also provided. In certain aspects, provided are methods that include administering to an individual having a cell proliferative disorder a therapeutically effective amount of an antibody of the present disclosure, where the antibody is administered to the individual to enhance an immune response, e.g., a T cell response, to abnormally proliferating cells of the cell proliferative disorder. The antibodies are also useful in various diagnostic, and monitoring applications, which are also provided.

23 Claims, 7 Drawing Sheets

Specification includes a Sequence Listing.

Size Exclusion Chromatography

| antibody | % Aggregation |
|---|---|
| MUC1 gB06 | 0.54% |
| MUC1 G12 | 0.14% |
| MUC1 H02 | 1.01% |

SEQUENCE LISTING

```
<160> NUMBER OF SEQ ID NOS: 46

<210> SEQ ID NO 1
<211> LENGTH: 117
<212> TYPE: PRT
<213> ORGANISM: Artificial sequence
<220> FEATURE:
<223> OTHER INFORMATION: synthetic sequence

<400> SEQUENCE: 1

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Met His Trp Ile Lys Gln Arg Pro Gly Lys Gly Leu Glu Trp Met
        35                  40                  45

Gly Tyr Phe Tyr Pro Arg Asp Asp Ser Thr Asn Tyr Asn Glu Lys Phe
    50                  55                  60

Lys Gly Arg Val Thr Leu Thr Ala Asp Lys Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Leu Arg Tyr Ala Leu Asp Tyr Trp Gly Gln Gly Thr Leu
            100                 105                 110

Val Thr Val Ser Ser
        115

<210> SEQ ID NO 2
<211> LENGTH: 108
<212> TYPE: PRT
<213> ORGANISM: Artificial sequence
<220> FEATURE:
<223> OTHER INFORMATION: synthetic sequence

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Gly Thr Ser Asn Leu Ala Ser Gly Val Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Ala Ala Val Tyr Tyr Cys His Gln Tyr Ala Trp Ser Pro
                85                  90                  95

Pro Thr Phe Gly Gln Gly Thr Lys Leu Glu Ile Lys
            100                 105

<210> SEQ ID NO 3
<211> LENGTH: 108
<212> TYPE: PRT
<213> ORGANISM: Artificial sequence
<220> FEATURE:
<223> OTHER INFORMATION: synthetic sequence

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Gly Ser Ser
            20                  25                  30

Asn Leu Tyr Trp Tyr Gln Gln Lys Pro Gly Gln Ala Pro Arg Leu Trp
        35                  40                  45

Ile Tyr Arg Ser Thr Lys Leu Ala Ser Gly Val Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Ala Ala Val Tyr Tyr Cys His Gln Tyr Arg Trp Ser Pro
                85                  90                  95

Pro Thr Phe Gly Gln Gly Thr Lys Leu Glu Ile Lys
            100                 105

<210> SEQ ID NO 4
<211> LENGTH: 108
<212> TYPE: PRT
<213> ORGANISM: Artificial sequence
<220> FEATURE:
<223> OTHER INFORMATION: synthetic sequence
```

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Ile Gly Thr Ser Asn Leu Ala Ser Gly Val Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Ala Ala Val Tyr Tyr Cys His Gln Tyr Ser Trp Ser Pro
                85                  90                  95

Pro Thr Phe Gly Gln Gly Thr Lys Leu Glu Ile Lys
            100                 105
```

<210> SEQ ID NO 5
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is Cys or Ser

<400> SEQUENCE: 5

```
Leu Xaa Thr Pro Ser Arg
1               5
```

<210> SEQ ID NO 6
<211> LENGTH: 6
<212> TYPE: PRT
<213> ORGANISM: Artificial sequence
<220> FEATURE:
<223> OTHER INFORMATION: synthetic sequence

<400> SEQUENCE: 6

```
Leu Cys Thr Pro Ser Arg
1               5
```

<210> SEQ ID NO 7
<211> LENGTH: 7
<212> TYPE: PRT
<213> ORGANISM: Artificial sequence
<220> FEATURE:
<223> OTHER INFORMATION: synthetic sequence

<400> SEQUENCE: 7

```
Gly Tyr Thr Phe Thr Asp His
1               5
```

<210> SEQ ID NO 8
<211> LENGTH: 6
<212> TYPE: PRT
<213> ORGANISM: Artificial sequence
<220> FEATURE:
<223> OTHER INFORMATION: synthetic sequence

<400> SEQUENCE: 8

```
Tyr Pro Arg Asp Asp Ser
1               5
```

<210> SEQ ID NO 9
<211> LENGTH: 8
<212> TYPE: PRT
<213> ORGANISM: Artificial sequence
<220> FEATURE:
<223> OTHER INFORMATION: synthetic sequence

<400> SEQUENCE: 9

Gly Leu Arg Tyr Ala Leu Asp Tyr
1               5

<210> SEQ ID NO 10
<211> LENGTH: 12
<212> TYPE: PRT
<213> ORGANISM: Artificial sequence
<220> FEATURE:
<223> OTHER INFORMATION: synthetic sequence

<400> SEQUENCE: 10

Arg Ala Ser Ser Ser Val Ser Ser Ser Tyr Leu Tyr
1               5                   10

<210> SEQ ID NO 11
<211> LENGTH: 7
<212> TYPE: PRT
<213> ORGANISM: Artificial sequence
<220> FEATURE:
<223> OTHER INFORMATION: synthetic sequence

<400> SEQUENCE: 11

Gly Thr Ser Asn Leu Ala Ser
1               5

<210> SEQ ID NO 12
<211> LENGTH: 9
<212> TYPE: PRT
<213> ORGANISM: Artificial sequence
<220> FEATURE:
<223> OTHER INFORMATION: synthetic sequence

<400> SEQUENCE: 12

His Gln Tyr Ala Trp Ser Pro Pro Thr
1               5

<210> SEQ ID NO 13
<211> LENGTH: 12
<212> TYPE: PRT
<213> ORGANISM: Artificial sequence
<220> FEATURE:
<223> OTHER INFORMATION: synthetic sequence

<400> SEQUENCE: 13

Arg Ala Ser Ser Ser Val Gly Ser Ser Asn Leu Tyr
1               5                   10

<210> SEQ ID NO 14
<211> LENGTH: 7
<212> TYPE: PRT
<213> ORGANISM: Artificial sequence
<220> FEATURE:
<223> OTHER INFORMATION: synthetic sequence

<400> SEQUENCE: 14

Arg Ser Thr Lys Leu Ala Ser
1               5

<210> SEQ ID NO 15
<211> LENGTH: 9
<212> TYPE: PRT
<213> ORGANISM: Artificial sequence
<220> FEATURE:
<223> OTHER INFORMATION: synthetic sequence

<400> SEQUENCE: 15

His Gln Tyr Arg Trp Ser Pro Pro Thr
1               5

<210> SEQ ID NO 16
<211> LENGTH: 9
<212> TYPE: PRT
<213> ORGANISM: Artificial sequence
<220> FEATURE:
<223> OTHER INFORMATION: synthetic sequence

<400> SEQUENCE: 16

His Gln Tyr Ser Trp Ser Pro Pro Thr
1               5

<210> SEQ ID NO 17
<211> LENGTH: 5
<212> TYPE: PRT
<213> ORGANISM: Artificial sequence
<220> FEATURE:
<223> OTHER INFORMATION: synthetic sequence

<400> SEQUENCE: 17

Asp His Thr Met His
1               5

<210> SEQ ID NO 18
<211> LENGTH: 17
<212> TYPE: PRT
<213> ORGANISM: Artificial sequence
<220> FEATURE:
<223> OTHER INFORMATION: synthetic sequence

<400> SEQUENCE: 18

Tyr Phe Tyr Pro Arg Asp Asp Ser Thr Asn Tyr Asn Glu Lys Phe Lys
1               5                   10                  15

Gly

<210> SEQ ID NO 19
<211> LENGTH: 351
<212> TYPE: DNA
<213> ORGANISM: Artificial sequence
<220> FEATURE:
<223> OTHER INFORMATION: synthetic sequence

<400> SEQUENCE: 19
gaggtccagc tggtacagtc tggggctgag gtgaagaagc ctggggctac agtgaaaatc      60
tcctgcaagg tttctggata caccttcacc gaccatacca tgcactggat caaacagcga     120
cctggaaaag gcttgagtg gatgggatac ttctacccta gagatgattc cacaaattac     180
aacgagaagt tcaagggcag agtcaccctt accgcggaca atctacaga cacagcctac     240 atggagctga gcagcctgag atctgaggac acggccgtgt attactgtgc gcgtggtctt     300
cgatacgctc ttgactactg gggccaagga accctggtca ccgtctcctc a             351

<210> SEQ ID NO 20
<211> LENGTH: 1255

<212> TYPE: PRT
<213> ORGANISM: Homo sapiens

<400> SEQUENCE: 20

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
            50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
370                 375                 380

Arg Pro Ala Pro Gly Ser Thr Ala Pro Pro Ala His Gly Val Thr Ser
385                 390                 395                 400
```

```
Ala Pro Asp Thr Arg Pro Ala Pro Gly Ser Thr Ala Pro Pro Ala His
            405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
            450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
            485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
            530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
            565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
            610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
            645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
            690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
            725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
            770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
            805                 810                 815
```

```
Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
        850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
        930                 935                 940

Arg Pro Ala Leu Gly Ser Thr Ala Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp  Thr Pro Thr Thr Leu  Ala Ser His
            995                 1000                 1005

Ser Thr  Lys Thr Asp Ala Ser  Ser Thr His His Ser  Ser Val Pro
    1010                 1015                 1020

Pro Leu  Thr Ser Ser Asn His  Ser Thr Ser Pro Gln  Leu Ser Thr
    1025                 1030                 1035

Gly Val  Ser Phe Phe Leu  Ser Phe His Ile Ser  Asn Leu Gln
    1040                 1045                 1050

Phe Asn  Ser Ser Leu Glu Asp  Pro Ser Thr Asp Tyr  Tyr Gln Glu
    1055                 1060                 1065

Leu Gln  Arg Asp Ile Ser Glu  Met Phe Leu Gln Ile  Tyr Lys Gln
    1070                 1075                 1080

Gly Gly  Phe Leu Gly Leu Ser  Asn Ile Lys Phe Arg  Pro Gly Ser
    1085                 1090                 1095

Val Val  Val Gln Leu Thr Leu  Ala Phe Arg Glu Gly  Thr Ile Asn
    1100                 1105                 1110

Val His  Asp Val Glu Thr Gln  Phe Asn Gln Tyr Lys  Thr Glu Ala
    1115                 1120                 1125

Ala Ser  Arg Tyr Asn Leu Thr  Ile Ser Asp Val Ser  Val Ser Asp
    1130                 1135                 1140

Val Pro  Phe Pro Phe Ser Ala  Gln Ser Gly Ala Gly  Val Pro Gly
    1145                 1150                 1155

Trp Gly  Ile Ala Leu Leu Val  Leu Val Cys Val Leu  Val Ala Leu
    1160                 1165                 1170

Ala Ile  Val Tyr Leu Ile Ala  Leu Ala Val Cys Gln  Cys Arg Arg
    1175                 1180                 1185

Lys Asn  Tyr Gly Gln Leu Asp  Ile Phe Pro Ala Arg  Asp Thr Tyr
    1190                 1195                 1200

His Pro  Met Ser Glu Tyr Pro  Thr Tyr His Thr His  Gly Arg Tyr
    1205                 1210                 1215

Val Pro  Pro Ser Ser Thr Asp  Arg Ser Pro Tyr Glu  Lys Val Ser
```

```
              1220                1225                1230
Ala Gly Asn Gly Gly Ser Ser Leu Ser Tyr Thr Asn Pro Ala Val
         1235                1240                1245

Ala Ala Thr Ser Ala Asn Leu
    1250            1255

<210> SEQ ID NO 21
<211> LENGTH: 5
<212> TYPE: PRT
<213> ORGANISM: Artificial sequence
<220> FEATURE:
<223> OTHER INFORMATION: synthetic sequence

<400> SEQUENCE: 21

Gly Ser Gly Gly Ser
1               5

<210> SEQ ID NO 22
<211> LENGTH: 4
<212> TYPE: PRT
<213> ORGANISM: Artificial sequence
<220> FEATURE:
<223> OTHER INFORMATION: synthetic sequence

<400> SEQUENCE: 22

Gly Gly Gly Ser
1

<210> SEQ ID NO 23
<211> LENGTH: 6
<212> TYPE: PRT
<213> ORGANISM: Artificial sequence
<220> FEATURE:
<223> OTHER INFORMATION: synthetic sequence

<400> SEQUENCE: 23

Leu Ser Thr Pro Ser Arg
1               5

<210> SEQ ID NO 24
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is 2-formylglycine

<400> SEQUENCE: 24

Leu Xaa Thr Pro Ser Arg
1               5

<210> SEQ ID NO 25
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is a
      2-formylglycine residue having a covalently attached moiety

<400> SEQUENCE: 25
```

```
Leu Xaa Thr Pro Ser Arg
1               5
```

<210> SEQ ID NO 26
<211> LENGTH: 20
<212> TYPE: PRT
<213> ORGANISM: Artificial sequence
<220> FEATURE:
<223> OTHER INFORMATION: synthetic sequence

<400> SEQUENCE: 26

```
Val Thr Ser Ala Pro Asp Thr Arg Pro Ala Pro Gly Ser Thr Ala Pro
1               5                   10                  15

Pro Ala His Gly
            20
```

<210> SEQ ID NO 27
<211> LENGTH: 60
<212> TYPE: PRT
<213> ORGANISM: Artificial sequence
<220> FEATURE:
<223> OTHER INFORMATION: synthetic sequence

<400> SEQUENCE: 27

```
Val Thr Ser Ala Pro Asp Thr Arg Pro Ala Pro Gly Ser Thr Ala Pro
1               5                   10                  15

Pro Ala His Gly Val Thr Ser Ala Pro Asp Thr Arg Pro Ala Pro Gly
            20                  25                  30

Ser Thr Ala Pro Pro Ala His Gly Val Thr Ser Ala Pro Asp Thr Arg
        35                  40                  45

Pro Ala Pro Gly Ser Thr Ala Pro Pro Ala His Gly
    50                  55                  60
```

<210> SEQ ID NO 28
<211> LENGTH: 20
<212> TYPE: PRT
<213> ORGANISM: Artificial sequence
<220> FEATURE:
<223> OTHER INFORMATION: synthetic sequence

<400> SEQUENCE: 28

```
Pro Leu Pro Val Thr Ser Thr Ser Ser Ala Ser Thr Gly His Ala Thr
1               5                   10                  15

Pro Leu Ala Val
            20
```

<210> SEQ ID NO 29
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is either present
      or absent and, when present, can be any amino acid though usually
      an aliphatic amino acid, a sulfur-containing amino acid, or a
      polar, uncharged amino acid
<220> FEATURE:
<221> NAME/KEY: SITE
<222> LOCATION: (2)..(2)
<223> OTHER INFORMATION: The amino acid at position 2 is cysteine or
      serine
<220> FEATURE:
<221> NAME/KEY: SITE
<222> LOCATION: (3)..(3)

```
<223> OTHER INFORMATION: The amino acid at position 3 can be any amino
      acid though usually an aliphatic amino acid, a polar, uncharged
      amino acid, or a sulfur containing amino acid
<220> FEATURE:
<221> NAME/KEY: SITE
<222> LOCATION: (4)..(4)
<223> OTHER INFORMATION: The amino acid at position 4 is proline or
      alanine
<220> FEATURE:
<221> NAME/KEY: SITE
<222> LOCATION: (5)..(5)
<223> OTHER INFORMATION: The amino acid at position 5 is any amino acid
      though usually an aliphatic amino acid, a polar, uncharged amino
      acid, or a sulfur containing amino acid
<220> FEATURE:
<221> NAME/KEY: SITE
<222> LOCATION: (6)..(6)
<223> OTHER INFORMATION: The amino acid at position 6 is a basic amino
      acid (e.g., Arg, Lys, His) or an aliphatic amino acid (e.g., Ala,
      Gly, Leu, Val, Ile, or Pro)

<400> SEQUENCE: 29

Xaa Xaa Xaa Xaa Xaa Xaa
1               5

<210> SEQ ID NO 30
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is either present
      or absent and, when present, is any amino acid
<220> FEATURE:
<221> NAME/KEY: SITE
<222> LOCATION: (2)..(2)
<223> OTHER INFORMATION: The amino acid at position 2 is 2-formylglycine
<220> FEATURE:
<221> NAME/KEY: SITE
<222> LOCATION: (3)..(3)
<223> OTHER INFORMATION: The amino acid at position 3 is any amino acid
<220> FEATURE:
<221> NAME/KEY: SITE
<222> LOCATION: (4)..(4)
<223> OTHER INFORMATION: The amino acid at position 4 is proline or
      alanine
<220> FEATURE:
<221> NAME/KEY: SITE
<222> LOCATION: (5)..(5)
<223> OTHER INFORMATION: The amino acid at position 5 is any amino acid
<220> FEATURE:
<221> NAME/KEY: SITE
<222> LOCATION: (6)..(6)
<223> OTHER INFORMATION: The amino acid at position 6 is a basic amino
      acid

<400> SEQUENCE: 30

Xaa Xaa Xaa Xaa Xaa Xaa
1               5

<210> SEQ ID NO 31
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is either present
      or absent and, when present, can be any amino acid, though usually
      an aliphatic amino acid, a sulfur-containing amino acid, or a
```

```
       polar, uncharged amino acid
<220> FEATURE:
<221> NAME/KEY: SITE
<222> LOCATION: (2)..(2)
<223> OTHER INFORMATION: The amino acid at position 2 is a
      2-formylglycine residue having a covalently attached moiety
<220> FEATURE:
<221> NAME/KEY: SITE
<222> LOCATION: (3)..(3)
<223> OTHER INFORMATION: The amino acid at position 3 is any amino acid,
      though usually an aliphatic amino acid, a sulfur-containing amino
      acid, or a polar, uncharged amino acid
<220> FEATURE:
<221> NAME/KEY: SITE
<222> LOCATION: (4)..(4)
<223> OTHER INFORMATION: The amino acid at position 4 is proline or
      alanine
<220> FEATURE:
<221> NAME/KEY: SITE
<222> LOCATION: (5)..(5)
<223> OTHER INFORMATION: The amino acid at position 5 is any amino acid
      though usually an aliphatic amino acid, a sulfur-containing amino
      acid, or a polar, uncharged amino acid
<220> FEATURE:
<221> NAME/KEY: SITE
<222> LOCATION: (6)..(6)
<223> OTHER INFORMATION: The amino acid at position 6 is a basic amino
      acid (e.g., Arg, Lys, His), or an aliphatic amino acid (e.g., Ala,
      Gly, Leu, Val, Ile, Pro)

<400> SEQUENCE: 31

Xaa Xaa Xaa Xaa Xaa Xaa
1               5

<210> SEQ ID NO 32
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(10)
<223> OTHER INFORMATION: Each amino acid at positions 3 to 10 may either
      be present or absent

<400> SEQUENCE: 32

Gly Gly Gly Gly Gly Gly Gly Gly Gly Gly
1               5                   10

<210> SEQ ID NO 33
<211> LENGTH: 7
<212> TYPE: PRT
<213> ORGANISM: Artificial sequence
<220> FEATURE:
<223> OTHER INFORMATION: synthetic sequence

<400> SEQUENCE: 33

Ser Ser Val Ser Ser Ser Tyr
1               5

<210> SEQ ID NO 34
<211> LENGTH: 8
<212> TYPE: PRT
<213> ORGANISM: Artificial sequence
<220> FEATURE:
<223> OTHER INFORMATION: synthetic sequence

<400> SEQUENCE: 34

Gly Tyr Thr Phe Thr Asp His Thr
1               5
```

<210> SEQ ID NO 35
<211> LENGTH: 10
<212> TYPE: PRT
<213> ORGANISM: Artificial sequence
<220> FEATURE:
<223> OTHER INFORMATION: synthetic sequence

<400> SEQUENCE: 35

Cys Tyr Pro Tyr Asp Val Pro Asp Tyr Ala
1               5                   10

<210> SEQ ID NO 36
<211> LENGTH: 8
<212> TYPE: PRT
<213> ORGANISM: Artificial sequence
<220> FEATURE:
<223> OTHER INFORMATION: synthetic sequence

<400> SEQUENCE: 36

Asp Tyr Lys Asp Asp Asp Asp Lys
1               5

<210> SEQ ID NO 37
<211> LENGTH: 11
<212> TYPE: PRT
<213> ORGANISM: Artificial sequence
<220> FEATURE:
<223> OTHER INFORMATION: synthetic sequence

<400> SEQUENCE: 37

Cys Glu Gln Lys Leu Ile Ser Glu Glu Asp Leu
1               5                   10

<210> SEQ ID NO 38
<211> LENGTH: 324
<212> TYPE: DNA
<213> ORGANISM: Artificial sequence
<220> FEATURE:
<223> OTHER INFORMATION: synthetic sequence

<400> SEQUENCE: 38

```
gaaattgtgt tgacacagtc tccagccacc ctgtctttgt ctccagggga aagagccacc    60
ctctcctgca gggccagttc aagtgttagc agcagctact tatactggta ccagcagaaa   120
cctggccagg ctcccaggct ctggatctat ggtacctcca accttgcctc cggcgtccca   180
gcaaggttca gtggcagtgg gtctgggaca gactacactc tcaccatcag ctccctggag   240
cctgaagatg cggcagttta ttactgtcac caatacgcct ggtccccgcc gacgttcggc   300
caagggacca gttggaaat caaa                                           324
```

<210> SEQ ID NO 39
<211> LENGTH: 324
<212> TYPE: DNA
<213> ORGANISM: Artificial sequence
<220> FEATURE:
<223> OTHER INFORMATION: synthetic sequence

<400> SEQUENCE: 39

```
gaaattgtgt tgacacagtc tccagccacc ctgtctttgt ctccagggga aagagccacc    60
ctctcctgca gggccagttc aagtgttggc agcagcaact tatactggta ccagcagaaa   120
cctggccagg ctcccaggct ctggatctat aggtccacca acttgcctc cggcgtccca   180 gcaaggttca gtggcagtgg gtctgggaca gactacactc tcaccatcag ctccctggag   240
```

```
cctgaagatg cggcagttta ttactgtcac caatacagat ggtccccgcc gacgttcggc    300
caagggacca agttggaaat caaa                                           324
```

<210> SEQ ID NO 40
<211> LENGTH: 324
<212> TYPE: DNA
<213> ORGANISM: Artificial sequence
<220> FEATURE:
<223> OTHER INFORMATION: synthetic sequence

<400> SEQUENCE: 40

```
gaaattgtgt tgacacagtc tccagccacc ctgtctttgt ctccagggga aagagccacc     60
ctctcctgca gggccagttc aagtgttagc agcagctact tatactggta ccagcagaaa   120
cctggccagg ctcccaggct ctggatcatt ggtacctcca accttgcctc cggcgtccca   180
gcaaggttca gtggcagtgg gtctgggaca gactacactc tcaccatcag ctccctggag   240
cctgaagatg cggcagttta ttactgtcac caatactcct ggtccccgcc gacgttcggc   300
caagggacca agttggaaat caaa                                          324
```

<210> SEQ ID NO 41
<211> LENGTH: 13
<212> TYPE: PRT
<213> ORGANISM: Artificial sequence
<220> FEATURE:
<223> OTHER INFORMATION: synthetic sequence

<400> SEQUENCE: 41

Arg Ala Ser Ser Ser Val Gly Ser Ser Ser Tyr Leu Tyr
1               5                   10

<210> SEQ ID NO 42
<211> LENGTH: 11
<212> TYPE: PRT
<213> ORGANISM: Artificial sequence
<220> FEATURE:
<223> OTHER INFORMATION: synthetic sequence

<400> SEQUENCE: 42

Gly Arg Thr Ser Ser Thr Asn Lys Leu Ala Ser
1               5                   10

<210> SEQ ID NO 43
<211> LENGTH: 11
<212> TYPE: PRT
<213> ORGANISM: Artificial sequence
<220> FEATURE:
<223> OTHER INFORMATION: synthetic sequence

<400> SEQUENCE: 43

His Gln Tyr Ala Arg Ser Trp Ser Pro Pro Thr
1               5                   10

<210> SEQ ID NO 44
<211> LENGTH: 8
<212> TYPE: PRT
<213> ORGANISM: Artificial sequence
<220> FEATURE:
<223> OTHER INFORMATION: synthetic sequence

<400> SEQUENCE: 44

Phe Tyr Pro Arg Asp Asp Ser Thr
1               5

```
<210> SEQ ID NO 45
<211> LENGTH: 10
<212> TYPE: PRT
<213> ORGANISM: Artificial sequence
<220> FEATURE:
<223> OTHER INFORMATION: synthetic sequence

<400> SEQUENCE: 45

Ala Arg Gly Leu Arg Tyr Ala Leu Asp Tyr
1               5                   10

<210> SEQ ID NO 46
<211> LENGTH: 7
<212> TYPE: PRT
<213> ORGANISM: Artificial sequence
<220> FEATURE:
<223> OTHER INFORMATION: synthetic sequence

<400> SEQUENCE: 46

Ser Ser Val Gly Ser Ser Asn
1               5
```

US 11,970,546 B2

ANTIBODY SPECIFIC FOR MUCIN-1 AND METHODS OF USE THEREOF

CROSS-REFERENCE TO RELATED APPLICATIONS

This application claims benefit of priority to U.S. Provisional Application No. 63/059,497, filed Jul. 31, 2020, the disclosure of which is incorporated herein by reference.

INCORPORATION BY REFERENCE OF SEQUENCE LISTING PROVIDED AS TEXT FILE

A Sequence Listing is provided herewith as a text file, "RDWD-035 SEQ LIST_ST25.txt," created on Jul. 27, 2021 and having a size of 29 KB. The contents of the text file are incorporated by reference herein in their entirety.

INTRODUCTION

Mucin-1 (also referred to as Mucin 1 or MUC1) is a member of the mucin family. Mucins are 0-glycosylated proteins that play an essential role in forming protective mucous barriers on epithelial surfaces. MUC1 is expressed on the apical surface of epithelial cells that line the mucosal surfaces of many different tissues including lung, breast, stomach and pancreas. This protein is proteolytically cleaved into alpha and beta subunits that form a heterodimeric complex. The N-terminal alpha subunit functions in cell-adhesion and the C-terminal beta subunit is involved in cell signaling. Overexpression, aberrant intracellular localization, and changes in glycosylation of this protein have been associated with carcinomas.

There is a need in the art for safe and effective agents that target MUC1 for the diagnosis and treatment of MUC1-associated conditions, such as cancer.

SUMMARY

The present disclosure provides antibodies specific for MUC1. Nucleic acids that encode one or both of the variable chain polypeptides of an antibody of the present disclosure are also provided, as are cells that include such nucleic acids. Also provided are compositions that include the antibodies of the present disclosure, including in some instances, pharmaceutical compositions. Methods of making and using the antibodies of the present disclosure are also provided. In certain aspects, provided are methods that include administering to an individual having a cell proliferative disorder a therapeutically effective amount of an antibody of the present disclosure, where the antibody is administered to the individual to enhance an immune response, e.g., a T cell response, to abnormally proliferating cells of the cell proliferative disorder. The antibodies are useful in various diagnostic, and monitoring applications, which are also provided.

DEFINITIONS

Figures 1, 2A:
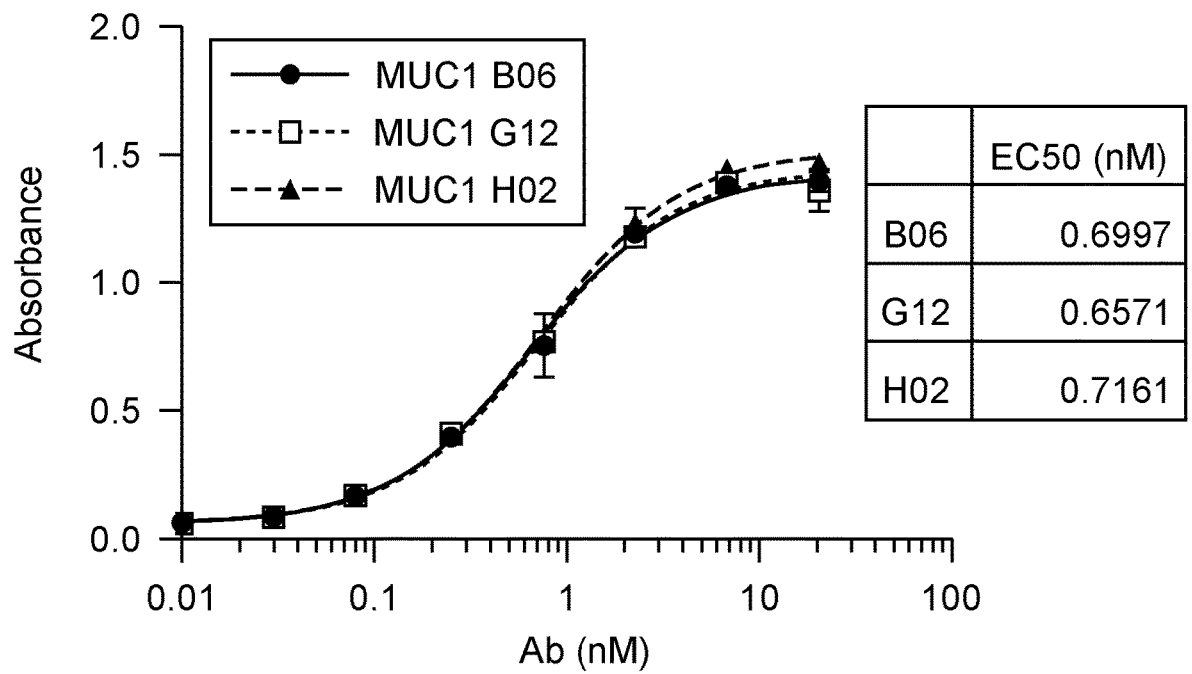
FIG. 1 shows that anti-MUC1 antibodies, MUC1 gB06, MUC1 G12, and MUC1 H02 are more than 99%, more than 99%, and more than 98% monomeric, respectively, as determined by size exclusion chromatography (SEC).
FIGS. 2A-2C show that anti-MUC1 antibodies, MUC1 gB06, MUC1 G12, and MUC1 H02 bind to recombinant 20mer MUC1 glycosylated-biotin but not to recombinant 60mer MUC1 non-glycosylated-biotin or to a glycosylated decoy peptide as assessed by ELISA.

The terms "antibodies" and "immunoglobulin" include antibodies or immunoglobulins of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies (e.g., scFv); fragments of antibodies (e.g., fragments of whole or single chain antibodies) which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent. "Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. In some aspects, the Fv polypeptide further comprises a polypeptide linker between the VH and VL domains, which enables the sFv to form the desired structure for antigen binding.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-MUC1 antibody binds specifically to an epitope within a MUC1 polypeptide, e.g., a human MUC1 polypeptide, for example, a glycosylated MUC1 or a fragment thereof. Non-specific binding would refer to binding with an affinity of less than about $10^{-7}$ M, e.g., binding with an affinity of $10^{-6}$ M, $10^{-5}$ M, $10^{-4}$ M, etc.

The term "specifically binds" in the context of an antibody and an antigen means that the antibody binds to or associates with the antigen with an affinity or $K_a$ (that is, an equilibrium association constant of a particular binding interaction with units of 1/M) of, for example, greater than or equal to about $10^5$ $M^{-1}$.

"High affinity" binding refers to binding with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater. Alternatively, affinity may be defined as an equilibrium dissociation constant ($K_D$) of a particular binding interaction with units of M (e.g., $10^{-5}$ M to $10^{-13}$ M, or less). In some embodiments, specific binding means the antibody binds to the antigen with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$M, or $10^{-12}$ M or less. The binding affinity of the antibody for an antigen can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by radioimmunoassay; or the like.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra Throughout the present disclosure, the numbering of the residues in an immunoglobulin heavy chain and in an immunoglobulin light chain is that as in Kabat et al., Sequences of Proteins of Immunological Interest, 5th Ed. Public Health Service, National Institutes of Health, Bethesda, Md. (1991), expressly incorporated herein by reference.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a μ or an ε heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins immediately after (C-terminal to) the light chain variable (VL) region, and is about 100 amino acids to 120 amino acids in length.

An "epitope" is a site on an antigen (e.g., a site on MUC1) to which an antibody binds. Epitopes can be formed both from contiguous amino acids or noncontiguous amino acids juxtaposed by folding (e.g., tertiary folding) of a protein. Epitopes formed from contiguous amino acids are typically retained on exposure to denaturing solvents whereas epitopes formed by folding are typically lost on treatment with denaturing solvents. An epitope typically includes at least 3, and more usually, at least 5 or 8-10 amino acids in a linear or spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996). Several commercial laboratories offer epitope mapping services. Epitopes bound by an antibody immunoreactive with a membrane associated antigen can reside on the surface of the cell (e.g. in the extracellular region of a transmembrane protein), so that such epitopes are considered cell-surface accessible, solvent accessible, and/or cell-surface exposed.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell, e.g., a mammalian host cell. These elements may include, but are not limited to: a promoter, a minimal promoter, an enhancer, a response element, a terminator sequence, a polyadenylation sequence, and the like.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting, veneering or resurfacing, chain shuffling, and the like. In certain embodiments, framework substitutions are identified by modeling of the interactions of the CDR and framework residues to identify framework residues important for antigen binding and sequence comparison to identify unusual framework residues at particular positions. Accordingly, the antibodies described above may be humanized using methods that are well known in the art.

In certain embodiments, the antibody molecules disclosed herein include a heavy chain comprising a variable heavy chain region as provided herein and a human IgG1 constant region having the amino acid sequence sequence set forth in UniProt: P01857-1, version 1. In certain embodiments, the antibody molecules disclosed herein include a light chain comprising a variable light chain region as provided herein and a human light chain constant region. In certain embodiments, the human light chain constant region is a human kappa light chain constant region having the amino acid set forth in UniProtKB/Swiss-Prot: P01834.2. In certain embodiments, the human IgG1 heavy chain constant region present in the subject antibodies may include mutations, e.g., substitutions to modulate Fc function. For example, the LALAPG effector function mutations (L234A, L235A, and P329G) or the N297A mutation may be introduced to reduce antibody dependent cellular cytotoxicity (ADCC). The numbering of the substitutions is based on the EU numbering system. The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, Md. (1991)). The "EU index as in Kabat" refers to the residue numbering of the human IgG 1 EU antibody.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like. In the context of an antibody, it is clear that a chain or a domain comprises a polypeptide.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "conjugated" generally refers to a chemical linkage, either covalent or non-covalent, usually covalent, that proximally associates one molecule of interest with a second molecule of interest. In some embodiments, the agent is selected from a half-life extending moiety, a labeling agent, and a therapeutic agent. For half-life extension, for example, the antibodies of the present disclosure can optionally be modified to provide for improved pharmacokinetic profile (e.g., by PEGylation, hyperglycosylation, and the like). Modifications that can enhance serum half-life are of interest.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a subject anti-MUC1 Ab that, when administered to a mammal or other subject for treating a disease, is sufficient to effect such treatment for the disease. The "therapeutically effective amount" will vary depending on the anti-MUC1 Ab, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. In some cases, a biological sample will include hepatic cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the CDR" includes reference to one or more CDRs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibodies specific for MUC1. Nucleic acids that encode one or both of the variable chain polypeptides of an antibody of the present disclosure are also provided, as are cells that include such nucleic acids. Also provided are compositions that include the antibodies of the present disclosure, including in some instances, pharmaceutical compositions. Methods of making and using the antibodies of the present disclosure are also provided. In certain aspects, provided are methods that include administering to an individual having a cell proliferative disorder a therapeutically effective amount of an antibody of the present disclosure, where the antibody is administered to the individual to enhance an immune response, e.g., a T cell response, to abnormally proliferating cells of the cell proliferative disorder. The antibodies are useful in various diagnostic, and monitoring applications, which are also provided.

MUC1 Antibodies

As summarized above, the present disclosure provides anti-MUC1 antibodies.

According to some embodiments, an antibody of the present disclosure specifically binds to MUC1 and competes for binding to MUC1 with an antibody comprising:

a variable heavy chain (VH) chain comprising heavy chain CDRs1-3 (HCDRs1-3) of a VH chain having the sequence:

(SEQ ID NO: 1)
EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYCAR

GLRYALDYWGQGTLVTVSS;

and a variable light chain (VL) chain comprising light chain CDRs1-3 (LCDRs1-3) of a VL chain having the sequence:

(SEQ ID NO: 2)
EIVLTQSPATLSLSPGERATLSCRASSSVSSSYLYWYQQKPGQAPRLWIY

GTSNLASGVPARFSGSGSGTDYTLTISSLEPEDAAVYYCHQYAWSPPTFG

QGTKLEIK;

(SEQ ID NO: 3)
EIVLTQSPATLSLSPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK;

or

```
                                              (SEQ ID NO: 4)
EIVLTQSPATLSLPGERATLSCRASSSVSSSYLYWYQQKPGQAPRLWII

GTSNLASGVPARFSGSGSGTDYTLTISSLEPEDAAVYYCHQYSWSPPTFG

QGTKLEIK.
```

Any suitable approach for determining whether a first antibody competes with a second antibody for binding to MUC1 may be employed. Whether a first antibody "competes with" a second antibody for binding to MUC1 may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is added. One of the two antibodies is labelled. If the labeled antibody and the unlabeled antibody bind to separate and discrete sites on MUC1, the labeled antibody will bind to the same level whether or not the suspected competing antibody is present. However, if the sites of interaction are identical or overlapping, the unlabeled antibody will compete, and the amount of labeled antibody bound to MUC1 will be lowered. If the unlabeled antibody is present in excess, very little, if any, labeled antibody will bind.

For purposes of the present disclosure, competing antibodies are those that decrease the binding of an antibody to MUC1 by about 50% or more, about 60% or more, about 70% or more, about 80% or more, about 85% or more, about 90% or more, about 95% or more, or about 99% or more. Details of procedures for carrying out such competition assays are well known in the art. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the antigen may be titrated. The results may be plotted, and the concentrations necessary to achieve the desired degree of binding inhibition may be compared.

According to some embodiments, an antibody of the present disclosure specifically binds to MUC1 and comprises:

a variable heavy chain (VH) chain comprising heavy chain CDRs1-3 (HCDRs1-3) of a VH chain having the sequence:

```
                                              (SEQ ID NO: 1)
EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYCAR

GLRYALDYWGQGTLVTVSS;
```
and a variable light chain (VL) chain comprising light chain CDRs1-3 (LCDRs1-3) of a VL chain having the sequence:

```
                                              (SEQ ID NO: 2)
EIVLTQSPATLSLPGERATLSCRASSSVSSSYLYWYQQKPGQAPRLWIY

GTSNLASGVPARFSGSGSGTDYTLTISSLEPEDAAVYYCHQYAWSPPTFG

QGTKLEIK;
```

```
                                              (SEQ ID NO: 3)
EIVLTQSPATLSLPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK;
or (SEQ ID NO: 4)
EIVLTQSPATLSLPGERATLSCRASSSVSSSYLYWYQQKPGQAPRLWII

GTSNLASGVPARFSGSGSGTDYTLTISSLEPEDAAVYYCHQYSWSPPTFG

QGTKLEIK.
```

The HCDRs1-3 and LCDRs1-3 may be as defined by Chothia, Kabat, or IMT nomenclature. The HCDRs1-3 of the anti-MUC1 antibodies disclosed herein as defined per the listed nomenclatures may be as follows:

TABLE 2

| Anti-MUC1 Antibody | Chothia | Kabat | IMGT |
|---|---|---|---|
| HCDR1 | GYTFTDH (SEQ ID NO: 7) | DHTMH (SEQ ID NO: 17) | GYTFTDHT (SEQ ID NO: 34) |
| HCDR2 | YPRDDS (SEQ ID NO: 8) | YFYPRDDSTNYNEKFKG (SEQ ID NO: 18) | FYPRDDST (SEQ ID NO: 44) |
| HCDR3 | GLRYALDY (SEQ ID NO: 9) | GLRYALDY (SEQ ID NO: 9) | ARGLRYALDY (SEQ ID NO: 45) |

The LCDRs1-3 of the anti-MUC1 antibodies disclosed herein may be as defined per the nomenclatures listed in Tables 3-5.

TABLE 3

| Anti-MUC1 Antibody | Chothia and Kabat | IMGT |
|---|---|---|
| LCDR1 | RASSSVSSSYLY (SEQ ID NO: 10) | SSVSSSY (SEQ ID NO: 33) |
| LCDR2 | GTSNLAS (SEQ ID NO: 11) | GT |
| LCDR3 | HQYAWSPPT (SEQ ID NO: 12) | HQYAWSPPT (SEQ ID NO: 12) |

TABLE 4

| Anti-MUC1 Antibody | Chothia and Kabat | IMGT |
|---|---|---|
| LCDR1 | RASSSVGSSNLY (SEQ ID NO: 13) | SSVGSSN (SEQ ID NO: 46) |
| LCDR2 | RSTKLAS (SEQ ID NO: 14) | RS |
| LCDR3 | HQYRWSPPT (SEQ ID NO: 15) | HQYRWSPPT (SEQ ID NO: 15) |

TABLE 5

| Anti-MUC Antibody | Chothia and Kabat | IMGT |
|---|---|---|
| LCDR1 | RASSSVSSSYLY (SEQ ID NO: 10) | SSVSSSY (SEQ ID NO: 33) |
| LCDR2 | GTSNLAS (SEQ ID NO: 11) | GT |
| LCDR3 | HQYSWSPPT (SEQ ID NO: 16) | HQYSWSPPT (SEQ ID NO: 16) |

In certain embodiments, the VH chain of an anti-MUC1 antibody comprises the HCDRs1-3 as set forth herein and the VL chain of the anti-MUC1 antibody comprises LCDRs1-3, wherein The LCDR1 comprises the amino acid sequence RASSSVG/SSSYLY (SEQ ID NO:41);

the LCDR2 comprises the amino acid sequence G/RT/SS/TN/KLAS (SEQ ID NO:42);

the LCDR3 comprises the amino acid sequence HQYA/R/SWSPPT (SEQ ID NO:43), as per Kabat definition.

In certain embodiments, the VH chain of an anti-MUC1 antibody comprises the HCDRs1-3 as set forth herein and comprises an amino acid sequence having 80% or greater, 85% or greater, 90% or greater, 95% or greater, 99% or greater, or 100% sequence identity to the amino acid sequence set forth in SEQ ID NO:1. In certain embodiments, any amino acid differences between the VH chain of an anti-MUC1 antibody of the present disclosure and SEQ ID NO:1 may be limited to regions outside of the CDRs, e.g., in one or more of the framework regions (FR), e.g., FR1, FR2, FR3, and/or FR4.

In certain embodiments, the VL chain of an anti-MUC1 antibody comprises the LCDRs1-3 as set forth herein in Table 3 and comprises an amino acid sequence having 80% or greater, 85% or greater, 90% or greater, 95% or greater, 99% or greater, or 100% sequence identity to the amino acid sequence set forth in SEQ ID NO:2.

In certain embodiments, the VL chain of an anti-MUC1 antibody comprises the LCDRs1-3 as set forth herein in Table 4 and comprises an amino acid sequence having 80% or greater, 85% or greater, 90% or greater, 95% or greater, 99% or greater, or 100% sequence identity to the amino acid sequence set forth in SEQ ID NO:3.

In certain embodiments, the VL chain of an anti-MUC1 antibody comprises the LCDRs1-3 as set forth herein in Table 5 and comprises an amino acid sequence having 80% or greater, 85% or greater, 90% or greater, 95% or greater, 99% or greater, or 100% sequence identity to the amino acid sequence set forth in SEQ ID NO:4.

In certain embodiments, any amino acid differences between the VL chain of an anti-MUC1 antibody of the present disclosure and SEQ ID NO:2, 3, and 4 may be limited to regions outside of the CDRs, e.g., in one or more of the framework regions (FR), e.g., FR1, FR2, FR3, and/or FR4.

In certain embodiments, an anti-MUC1 antibody of the present disclosure can comprise: a) a heavy chain comprising a VH region having the amino acid sequence set forth in SEQ ID NO:1; and a light chain comprising the VL region having the amino acid sequence set forth in SEQ ID NO:2, 3, or 4.

The anti-MUC1 antibodies of the present disclosure may bind to MUC-1 with an EC50 of about 0.4-1 nM, e.g., 0.5-0.9 nM, 0.6-0.8 nM, or 0.65-0.75 nM as measured by ELISA. The concentration of an antibody that provides half maximal response (e.g., half of the maximum fluorescence intensity) is measured as the EC50. The MUC-1 may be the 20mer glycosylated MUC1 peptide as disclosed in Example 1.

The anti-MUC1 antibodies of the present disclosure may bind to 20mer MUC1 glycosylated peptide but not to recombinant 60mer MUC1 non-glycosylated peptide, as disclosed in Example 1.

The anti-MUC1 antibodies of the present disclosure may bind to cancerous tissue and may show no binding (e.g., insignificant binding as measured by immunohistochemistry or binding undetectable by immunohistochemistry) to normal tissue. For example, the anti-MUC1 antibodies described herein may bind to human gastric, breast, and/or lung tissue that have cancerous cells while showing no detectable binding to human gastric, breast, and/or lung tissue that do not have cancerous cells.

In certain embodiments, the VH region of an anti-MUC1 antibody of the present disclosure is encoded by a nucleic acid having at least 50%, at least 60%, at least 70%, at least 80%, at least 90%, at least 95%, or a 100% sequence identity to the nucleic acid sequence:

(SEQ ID NO: 19)
GAGGTCCAGCTGGTACAGTCTGGGGCTGAGGTGAAGAAGCCTGGGGC

TACAGTGAAAATCTCCTGCAAGGTTTCTGGATACACCTTCACCGACCATA

CCATGCACTGGATCAAACAGCGACCTGGAAAAGGGCTTGAGTGGATGGGA

TACTTCTACCCTAGAGATGATTCCACAAATTACAACGAGAAGTTCAAGGG

CAGAGTCACCCTTACCGCGGACAAATCTACAGACACAGCCTACATGGAGC

TGAGCAGCCTGAGATCTGAGGACACGGCCGTGTATTACTGTGCGCGTGGT

CTTCGATACGCTCTTGACTACTGGGGCCAAGGAACCCTGGTCACCGTCTC

CTCA

In certain embodiments, the VL region of an anti-MUC1 antibody of the present disclosure is encoded by a nucleic acid having at least 50%, at least 60%, at least 70%, at least 80%, at least 90%, at least 95%, or a 100% sequence identity to the nucleic acid sequence:

(SEQ ID NO: 38)
GAAATTGTGTTGACACAGTCTCCAGCCACCCTGTCTTTGTCTCCAGGG

GAAAGAGCCACCCTCTCCTGCAGGGCCAGTTCAAGTGTTAGCAGCAGCTA

CTTATACTGGTACCAGCAGAAACCTGGCCAGGCTCCCAGGCTCTGGATCT

ATGGTACCTCCAACCTTGCCTCCGGCGTCCCAGCAAGGTTCAGTGGCAGT

GGGTCTGGGACAGACTACACTCTCACCATCAGCTCCCTGGAGCCTGAAGA

TGCGGCAGTTTATTACTGTCACCAATACGCCTGGTCCCCGCCGACGTTCG

GCCAAGGGACCAAGTTGGAAATCAAA;

(SEQ ID NO: 39)
GAAATTGTGTTGACACAGTCTCCAGCCACCCTGTCTTTGTCTCCAGGG

GAAAGAGCCACCCTCTCCTGCAGGGCCAGTTCAAGTGTTGGCAGCAGCAA

CTTATACTGGTACCAGCAGAAACCTGGCCAGGCTCCCAGGCTCTGGATCT

ATGGTCCACCAAACTTGCCTCCGGCGTCCCAGCAAGGTTCAGTGGCAGT

GGGTCTGGGACAGACTACACTCTCACCATCAGCTCCCTGGAGCCTGAAGA

-continued

```
TGCGGCAGTTTATTACTGTCACCAATACAGATGGTCCCCGCCGACGTTCG

GCCAAGGGACCAAGTTGGAAATCAAA;
or
                                              (SEQ ID NO: 40)
GAAATTGTGTTGACACAGTCTCCAGCCACCCTGTCTTTGTCTCCAGGG

GAAAGAGCCACCCTCTCCTGCAGGGCCAGTTCAAGTGTTAGCAGCAGCTA

CTTATACTGGTACCAGCAGAAACCTGGCCAGGCTCCCAGGCTCTGGATCA

TTGGTACCTCCAACCTTGCCTCCGGCGTCCCAGCAAGGTTCAGTGGCAGT

GGGTCTGGGACAGACTACACTCTCACCATCAGCTCCCTGGAGCCTGAAGA

TGCGGCAGTTTATTACTGTCACCAATACTCCTGGTCCCCGCCGACGTTCG

GCCAAGGGACCAAGTTGGAAATCAAA.
```

The antibodies find use in a variety of research, diagnostic, and therapeutic applications, including for performing any of the methods described in U.S. Patent Application Nos. US20120141375A1, US20160145343A1, the disclosure of which is incorporated herein by reference in its entirety for all purposes.

A subject antibody specifically binds a MUC1 polypeptide, where the epitope comprises amino acid residues within a human MUC1 antigen comprising the amino acid sequence set forth in SEQ ID NO:20:

```
                                              (SEQ ID NO: 20)
MTPGTQSPFFLLLLLTVLTVVTGSGHASSTPGGEKETSATQRSSVPSSTE

KNAVSMTSSVLSSHSPGSGSSTTQGQDVTLAPATEPASGSAATWGQDVTS

VPVTRPALGSTTPPAHDVTSAPDNKPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDNRPALGS

TAPPVHNVTSASGSASGSASTLVHNGTSARATTTPASKSTPFSIPSHHSD

TPTTLASHSTKTDASSTHHSSVPPLTSSNHSTSPQLSTGVSFFFLSFHIS

NLQFNSSLEDPSTDYYQELQRDISEMFLQIYKQGGFLGLSNIKFRPGSVV

VQLTLAFREGTINVHDVETQFNQYKTEAASRYNLTISDVSVSDVPFPFSA

QSGAGVPGWGIALLVLVCVLVALAIVYLIALAVCQCRRKNYGQLDIFPAR

DTYHPMSEYPTYHTHGRYVPPSSTDRSPYEKVSAGNGGSSLSYTNPAVAA

TSANL
```

In certain embodiments, the MUC1 epitope bound by the anti-MUC1 antibodies disclosed herein is glycosylated. In certain embodiments, the MUC1 epitope bound by the anti-MUC1 antibodies disclosed herein is present on MUC1 expressed by epipulmonary adenocarcinoma cell lines and pulmonary epithelial cells.

A subject antibody exhibits high affinity binding to MUC1. For example, a subject antibody binds to MUC1 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on MUC1 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

An anti-MUC1 antibody of the present disclosure can in some cases induce apoptosis in a cell that expresses MUC1 on its cell surface.

A "MUC1 antigen" or "MUC1 polypeptide" can comprises an amino acid sequence having at least about 75%, at least about 80%, at least about 90%, at least about 95%, at least about 98%, at least about 99%, or 100%, amino acid sequence identity to SEQ ID NO:20.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to MUC1, as described above. Examples of binding fragments include (i) a Fab fragment (a monovalent fragment consisting of the VL, VH, CL and CH1 domains; (ii) a F(ab')₂ fragment (a bivalent fragment comprising two Fab fragments linked by a disulfide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

Full length bispecific antibodies may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope.

The "knob-in-hole" strategy (see, e.g., PCT Intl. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S/L368A/Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. U82010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351 Y/F405A/Y407T/T394W, T366I/K392M/T394W/F405A/Y407V, T366L/K392M/T394W/F405A/Y407V, L351Y/Y407A/T366A/K409F, L351Y/Y407A/T366V/K409F, Y407A/T366A/K409F, or T350V/L351Y/F405A/Y407V, T350V/T366L/K392L/T394W as described in U.S. Pat. Pub. No. US2012/0149876 or U.S. Pat. Pub. No. US2013/0195849.

Also provided are single chain bispecific antibodies. In some embodiments, a single chain bispecific antibody of the present disclosure is a bispecific scFv. A subject antibody can be humanized. The constant region(s), if present, can also be substantially or entirely from a human immunoglobulin.

Methods of making humanized antibodies are known in the art. The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIA-CORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity. The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196: 901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv (scFv$_2$)), an scFv trimer (e.g., comprises three tandem scFv (scFv$_3$)), an scFv tetramer (e.g., comprises four tandem scFv (scFv$_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., (Gly)$_x$, where x is an integer from 2 to 10, glycine-serine polymers, and the like.

In certain embodiments, the antibody is conjugated to the agent via a cleavable or a non-cleavable linker. Linkers suitable for use a subject antibody include "flexible linkers."

If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

According to some embodiments, the linker is a chemically-labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers, oxime-based linkers, carbonate-based linkers, ester-based linkers, etc. In certain embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., a cancer cell). Enzyme-labile linkers include, but are not limited to, linkers that include peptidic bonds, e.g., dipeptide-based linkers such as valine-citrulline (VC) linkers, such as a maleimidocaproyl-valine-citruline-p-aminobenzyl (MC-vc-PAB) linker, a valyl-alanyl-para-aminobenzyloxy (Val-Ala-PAB) linker, and the like.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')$_2$, and Fv, or as single chain antibodies in which heavy and light chain variable domains are linked through a spacer.

In some embodiments, an anti-MUC1 antibody of the present disclosure may include one or more amino acid substitutions introduced in the Fc region. In some embodiments, the one or more of the amino acid substitutions may be at the positions 239, 298, 326, 330 and 332 in the Fc region. In some embodiments, an anti-MUC1 antibody of the present disclosure may include one or more of the following amino acid substitutions introduced in the Fc region: I332E; S239D/A330L/I332E; S239D/S298A/I332E; S239D/K326T/I332E; S239D/S298A/K326T/I332E; or S239D/A330L/I332E/D356E/L358M.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. Inclusion of a non-naturally occurring amino acid can provide for linkage to a polymer, a second polypeptide, a scaffold, etc. Examples of such non-naturally-occurring amino acids include, but are not limited to, N-acetylglucosaminyl-L-serine, N-acetylglucosaminyl-L-threonine, and O-phosphotyrosine.

The present disclosure also provides anti-MUC1 antibodies having an attached moiety of interest, e.g. a detectable label, drug, half-life-extending moiety, and the like. Modification of antibodies can be accomplished by a variety of synthetic and/or recombinant methods. The moiety or moieties attached to an antibody can provide for one or more of a wide variety of functions or features. Exemplary moieties include detectable labels (e.g., dye labels (e.g., chromophores, fluorophores), biophysical probes (spin labels, nuclear magnetic resonance (NMR) probes), fluorescence Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like); water soluble polymers (e.g., PEGylation); purification tags (e.g., to facilitate isolation by affinity chromatography (e.g., attachment of a FLAG epitope; membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); and the like.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

In some embodiments, a subject antibody is covalently linked to a PEG polymer. In some embodiments, a subject scFv multimer is covalently linked to a PEG polymer. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons. The PEG conjugated to the subject antibody can be linear or branched. Branched PEG derivatives include star-PEG's and multi-armed PEG's.

A subject antibody can be glycosylated, e.g., a subject antibody can comprise a covalently linked carbohydrate or polysaccharide moiety. Glycosylation of antibodies is typically either N-linked or O-linked. Addition of glycosylation sites to an antibody is conveniently accomplished by altering the amino acid sequence such that it contains N- or O-linked glycosylation sites. Similarly, removal of glycosylation sites can be accomplished by amino acid alteration within the native glycosylation sites of an antibody.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties.

Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody can in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^{3}$H $^{125}$I, $^{35}$S $^{14}$C, or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use as a detectable label, e.g., in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals.

Suitable fluorescent proteins that can be linked to a subject antibody include, but are not limited to, a green fluorescent protein from *Aequoria victoria* or a mutant or derivative thereof, Enhanced GFP, many such GFP which are available commercially, e.g., from Clontech, Inc.; a red fluorescent protein; a yellow fluorescent protein; any of a variety of fluorescent and colored proteins from Anthozoan species; and the like.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives, radiopaque multiurethanes, organobismuth composites, radiopaque barium multimer complexes, and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, and the like; provide for secretion of the fusion protein from a cell; provide an epitope tag, e.g., (His)n, e.g., 6His, and the like; provide for secretion of the fusion protein from a cell; provide an epitope tag, e.g., GST, hemagglutinin (HA; e.g., CYPYDVPDYA; SEQ ID NO:35), FLAG (e.g., DYKDDDDK; SEQ ID NO:36), c-myc (e.g., CEQKLISEEDL; SEQ ID NO:37), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

In some embodiments, a subject antibody comprises a polyamine modification. A subject antibody can be modified with polyamines that are either naturally occurring or synthetic. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or N(R)$_2$ moieties, wherein R is H, (C1-C$_4$) alkyl, phenyl, or benzyl. Polyamines can be linked to an antibody using any standard crosslinking method.

Where an anti-MUC1 antibody of the present disclosure comprises a covalently linked heterologous moiety, the heterologous moiety can be linked to the anti-MUC1 heavy and/or light chain directly or via a linker. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Examples of flexible linkers include glycine polymers (G)n, glycine-serine polymers (including, for example, (GS)$_n$, (GSGGS)$_n$ (SEQ ID NO:21) and (GGGS). (SEQ ID NO:22), where n is an integer of at least one), glycine-alanine polymers, alanine-serine polymers, and other flexible linkers known in the art.

Methods for Modification of Antibodies

The antibodies can be modified to have a covalently attached heterologous moiety (e.g., detectable label, drug, etc.) by use of any of a variety of methods. The present disclosure provides an anti-MUC1 antibody conjugated to a moiety of interest, where an anti-MUC1 antibody conjugated to a moiety of interest is referred to as an "anti-MUC1 antibody conjugate." An anti-MUC1 antibody conjugate of the present disclosure can include: 1) Ig heavy chain constant region conjugated to a moiety of interest; and an Ig light chain constant region conjugated to a moiety of interest; 2) an Ig heavy chain constant region conjugated to a moiety of interest; and an Ig light chain constant region that is not conjugated to a moiety of interest; or 3) an Ig heavy chain constant region that is not conjugated to a moiety of interest; and an Ig light chain constant region conjugated to a moiety of interest. A subject anti-MUC1 antibody conjugate can also include VH and/or VL domains conjugated to a moiety of interest.

In one example, the antibody can be modified to include a 2-formylglycine residue, which can serve as a chemical handle for attachment of a heterologous moiety. For example, the heavy and/or light chain constant region of an anti-MUC1 of the present disclosure can be modified to include an amino acid sequence of a sulfatase motif which is capable of being converted by action of a 2-formylglycine generating enzyme (FGE) to contain a 2-formylglycine (fGly). Such sulfatase motifs may also be referred to herein as an FGE-modification site. Action of FGE is directed in a sequence-specific manner in that the FGE acts at a sulfatase motif positioned within the immunoglobulin polypeptide. The moiety of interest is provided as component of a reactive partner for reaction with an aldehyde of the fGly residue of a converted aldehyde tag of the tagged Ig polypeptide. A wide range of commercially available reagents can be used to accomplish attachment of a moiety of interest to an fGly residue of an aldehyde tagged Ig polypeptide. For example, aminooxy, hydrazide, or thiosemicarbazide derivatives of a number of moieties of interest are suitable reactive partners, and are readily available or can be generated using standard chemical methods.

For example, to attach a poly(ethylene glycol) (PEG) moiety to a tagged Ig polypeptide, an aminooxy-PEG can be generated from monoamino-PEGs and aminooxyglycine using standard protocols. The aminooxy-PEG can then be reacted with a converted (e.g., fGly-modified) aldehyde tagged Ig polypeptide to provide for attachment of the PEG moiety. Delivery of a biotin moiety to a converted aldehyde tagged polypeptide can be accomplished using aminooxy biotin, biotin hydrazide or 2,4 dinitrophenylhydrazine.

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length. In certain embodiments, the sulfatase motif used may be described by the formula:

$$X^1Z^1X^2Z^2X^3Z^3 \text{(SEQ ID NO:29)} \qquad \text{(I), where}$$

$Z^1$ is cysteine or serine (which can also be represented by (C/S));

$Z^2$ is either a proline or alanine residue (which can also be represented by (P/A));

$Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X^1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V, with the proviso that when the sulfatase motif is at the N-terminus of the target polypeptide, $X^1$ is present; and $X^2$ and $X^3$ independently can be any amino acid, though usually an aliphatic amino acid, a polar, uncharged amino acid, or a sulfur containing amino acid (i.e., other than a aromatic amino acid or a charged amino acid), e.g., S, T, A, V, G or C; e.g., S, T, A, V or G. In one example, the aldehyde tag is of the formula L(C/S)TPSR (SEQ ID NO:5), e.g., LCTPSR (SEQ ID NO:6) or LSTPSR (SEQ ID NO:23). Thus, the present disclosure provides antibodies that include an aldehyde-tagged Ig heavy chain and/or an aldehyde-tagged Ig light chain, where the aldehyde-tagged Ig antibody comprises an Ig constant region amino acid sequence of the heavy and/or light chain contains such a sulfatase motif.

In general, the FGE used to facilitate conversion of cysteine or serine to fGly in a sulfatase motif of an aldehyde tag of a target polypeptide is selected according to the sulfatase motif present in the aldehyde tag. The FGE can be native to the host cell in which the aldehyde tagged polypeptide is expressed, or the host cell can be genetically modified to express an appropriate FGE. In some embodiments it may be desired to use a sulfatase motif compatible with a human FGE, and express the aldehyde tagged protein in a human cell that expresses the FGE or in a host cell, usually a mammalian cell, genetically modified to express a human FGE. In general, an FGE suitable for use in generating an fGly-modified antibody can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily.

Following action of an FGE on the sulfatase motif, $Z_1$ is oxidized to generate a 2-formylglycine (fGly) residue. Furthermore, following both FGE-mediated conversion and reaction with a reactive partner comprising a moiety of interest, fGly position at $Z_1$ in the formula above is covalently bound to the moiety of interest (e.g., detectable label, water soluble polymer, polypeptide, drug, etc.). Thus, the present disclosure provides an anti-MUC1 antibody modified to comprise an fGly moiety, wherein the anti-MUC1 antibody comprises an fGly-converted sulfatase motif of the formula:

$$X^1(\text{fGly})X^2Z^2X^3Z^3 \qquad \text{(SEQ ID NO:30), wherein:}$$

$X^1$ is present or absent and, when present, is any amino acid, with the proviso that when the sulfatase motif is at an N-terminus of the polypeptide, $X^1$ is present;

$X^2$ and $X^3$ are each independently any amino acid; and $Z^2$ is either a proline or alanine residue (which can also be represented by (P/A));

$Z^3$ is a basic amino acid; and where the fGly-modified anti-MUC1 antibody presents the fGly group on a solvent-accessible surface when in a folded state. In some embodiments, the fGly-converted sulfatase motif is of the formula L(fGly)TPSR (SEQ ID NO:24).

As noted above, a subject anti-MUC1 antibody modified to include an fGly moiety can be further modified to include a heterologous moiety of interest (e.g., detectable label, water soluble polymer, polypeptide, drug, etc.) covalently bound to the anti-MUC1 antibody via the fGly moiety. Thus, the present disclosure provides an anti-MUC1 antibody conjugate (also referred to herein as an "anti-MUC1 conjugate"), the anti-MUC1 conjugate comprising:

$$X^1(\text{fGly}')X^2Z^2X^3Z^3 \qquad \text{(SEQ ID NO:31) (I'), where}$$

fGly' is the 2-formylglycine residue having a covalently attached moiety;

$Z^2$ is either a proline or alanine residue (which can also be represented by (P/A)); $Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X^1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M or V, with the proviso that when the sulfatase motif is at the N-terminus of the target polypeptide, $X^1$ is present; and $X^2$ and $X^3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G or C, more usually S, T, A, V or G. In some embodiments, the motif is of the formula L(fGly')TPSR (SEQ ID NO:25).

Drugs

In some cases, an anti-MUC1 antibody of the present disclosure comprises drug covalently linked to the heavy and/or light chain of the antibody. "Drugs" include small molecule drugs, peptidic drugs, toxins (e.g., cytotoxins), and the like.

"Small molecule drug" as used herein refers to a compound, e.g., an organic compound, which exhibits a pharmaceutical activity of interest and which is generally of a molecular weight of no greater than about 800 Da, or no greater than 2000 Da, but can encompass molecules of up to 5 kDa and can be as large as about 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a toxin, e.g., a cytotoxin. Ribosome inactivating proteins (RIPs), which are a class of proteins ubiquitous in higher plants, are examples of such cytotoxins. Suitable cytotoxins include, but are not limited to, ricin, abrin, diphtheria toxin, a *Pseudomonas* exotoxin (e.g., PE35, PE37, PE38, PE40, etc.), saporin, gelonin, a pokeweed anti-viral protein (PAP), botulinum toxin, bryodin, momordin, and bouganin.

In some cases, the drug is a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (*vinca*) alkaloids, and steroid hormones. Peptidic compounds can also be used.

Suitable cancer chemotherapeutic agents include dolastatin and active analogs and derivatives thereof; and auristatin and active analogs and derivatives thereof. Suitable cancer chemotherapeutic agents also include maytansinoids and active analogs and derivatives thereof; and duocarmycins and active analogs and derivatives thereof.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; aziridinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus* yannanensis).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives; piperazino and piperazino derivatives.

Methods of Producing Antibody

A subject antibody can be produced by any known method, e.g., conventional synthetic methods for protein synthesis; recombinant DNA methods, etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. Other microbes, such as yeast, are also useful for expression. *Saccharomyces* (e.g., *S. cerevisiae*) and *Pichia* are examples of suitable yeast host cells.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like.

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus;

mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator.

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Cells

The present disclosure provides isolated genetically modified host cells (e.g., in vitro cells) that are genetically modified with a subject nucleic acid. In some embodiments, a subject isolated genetically modified host cell can produce a subject antibody.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) 293 cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like.

Pharmaceutical Compositions

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in the number of cancerous cells. In some cases, the desired result is at least a reduction in a symptom of a malignancy, as compared to a control.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 nM to 500 nM.

In some embodiments, a subject formulation includes a subject antibody, and one or more agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(–)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Physical systems include, but are not limited to, reservoir systems with rate-controlling membranes, such as microencapsulation, macroencapsulation, and membrane systems;

reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrahepatic, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a breast cancer, pancreatic cancer, or lung cancer. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection, e.g., for systemic delivery (e.g., intravenous infusion) or to a local site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Treatment Methods

The present disclosure provides methods of treating a disease or disorder associated with or caused by a MUC1-positive cell, e.g., a cancerous MUC1-positive cell or an autoreactive MUC1-positive cell.

Treating Malignancies

The present disclosure provides methods of treating a malignancy, including a solid tumor or a hematologic malignancy, the methods generally involving administering to an individual in need thereof (e.g., an individual having a malignancy) an effective amount of a subject antibody, alone (e.g., in monotherapy) or in combination (e.g., in combination therapy) with one or more additional therapeutic agents.

Malignancies include, e.g., HCC, non-Hodgkin's lymphoma, Burkitt's lymphoma, multiple myeloma, chronic lymphocytic leukemia, hairy cell leukemia, prolymphocytic leukemia, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, vulvar cancer, and the like.

In some embodiments, an effective amount of a subject antibody is an amount that, when administered alone (e.g., in monotherapy) or in combination (e.g., in combination therapy) with one or more additional therapeutic agents, in one or more doses, is effective to reduce the number of cancerous cells in an individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the number of cancerous cells in the individual in the absence of treatment with the antibody.

Combination Therapy

In some embodiments, a subject method of treating a malignancy involves administering a subject antibody and one or more additional therapeutic agents. Suitable additional therapeutic agents include, but are not limited to, a cancer chemotherapeutic agent (as described above).

Subjects Suitable for Treatment

A variety of subjects are suitable for treatment with a subject method. Suitable subjects include any individual, e.g., a human, who has a malignancy; who has been diagnosed with a malignancy; who has had a malignancy and is at risk for recurrence of the malignancy; who has been treated for a malignancy with an agent other than a subject anti-MUC1 antibody (e.g., who has been treated with a cancer chemotherapeutic agent) and who has not responded to the agent; or who has been treated for a malignancy with an agent other than a subject anti-MUC1 antibody (e.g., who has been treated with a cancer chemotherapeutic agent) and who initially responded to the agent but subsequently ceased to respond (e.g., relapsed).

Detection Methods

The present disclosure provides various detection methods that involve use of a subject antibody. Detection methods include diagnostic methods, prognostic methods, and monitoring methods. A subject detection method generally involves detecting MUC1 positive cells, e.g., cancerous cells.

In some embodiments, a subject method is a diagnostic method, e.g., to determine whether an individual has a malignancy.

In some embodiments, a subject method is a monitoring method, e.g., an individual who has been diagnosed as having a malignancy, and is being treated for the disorder, is monitored for response to the treatment and/or progression/regression of the disorder.

In some cases, a subject detection method involves administering to an individual a detectably labeled anti-MUC1 antibody of the present disclosure; and detecting binding of the antibody to tissues in the individual. Detection can be achieved, e.g., by magnetic resonance imaging or other suitable imaging technique.

In other instances, a subject detection method involves contacting a detectably labeled anti-MUC1 antibody of the present disclosure with a biological sample obtained from an individual; and detecting binding of the antibody to molecules in the biological sample.

The anti-MUC1 antibody can be labeled directly or indirectly. Indirect labels include a secondary antibody that comprises a detectable label, where the secondary antibody binds a subject anti-MUC1 antibody. Other indirect labels include biotin, where a biotinylated anti-MUC1 antibody can be detected using avidin or streptavidin that comprises a detectable label.

Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^{3}$H, $^{125}$I, $^{35}$S, $^{14}$C, or $^{32}$P), enzymes (e.g., horseradish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{1231}$I (iodine), $^{18}$F(fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. A subject antibody can be labeled with Gd by, for example, conjugating polylysine-Gd chelates to the antibody. Alternatively, a subject antibody can be labeled with Gd by incubating paramagnetic polymerized liposomes that include Gd chelator lipid with avidin and biotinylated antibody.

Suitable fluorescent proteins that can be linked to a subject antibody include, but are not limited to, a green fluorescent protein from *Aequoria victoria* or a mutant or derivative thereof, Enhanced GFP, many such GFP which are available commercially, e.g., from Clontech, Inc.; a red fluorescent protein; a yellow fluorescent protein; any of a variety of fluorescent and colored proteins from Anthozoan species; and the like.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-50 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An antibody that specifically binds to mucin-1 (MUC-1), and competes for binding to MUC-1 with a second antibody comprising:
   a variable heavy chain (VH) chain comprising heavy chain CDRs1-3 (HCDRs1-3) of a VH chain having the sequence:

(SEQ ID NO: 1)
   EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYC

ARGLRYALDYWGQGTLVTVSS;

and
   a variable light chain (VL) chain comprising light chain CDRs1-3 (LCDRs1-3) of a VL chain having the sequence:

(SEQ ID NO: 2)
   EIVLTQSPATLSLSPGERATLSCRASSSVSSSYLYWYQQKPGQAPRLWIY

GTSNLASGVPARFSGSGSGTDYTLTISSLEPEDAAVYYCHQYAWSPPTFG

QGTKLEIK;

(SEQ ID NO: 3)
   EIVLTQSPATLSLSPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK;
   or (SEQ ID NO: 4)
   EIVLTQSPATLSLSPGERATLSCRASSSVSSSYLYWYQQKPGQAPRLWII

GTSNLASGVPARFSGSGSGTDYTLTISSLEPEDAAVYYCHQYSWSPPTFG

QGTKLEIK.

2. An antibody that specifically binds to Mucin-1 (MUC-1), the antibody comprising:
   a variable heavy chain (VH) chain comprising heavy chain CDRs1-3 (HCDRs1-3) of a VH chain having the sequence:

(SEQ ID NO: 1)
   EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYC

ARGLRYALDYWGQGTLVTVSS;

and
   a variable light chain (VL) chain comprising light chain CDRs1-3 (LCDRs1-3) of a VL chain having the sequence:

(SEQ ID NO: 2)
   EIVLTQSPATLSLSPGERATLSCRASSSVSSSYLYWYQQKPGQAPRLWIY

GTSNLASGVPARFSGSGSGTDYTLTISSLEPEDAAVYYCHQYAWSPPTFG

QGTKLEIK;

(SEQ ID NO: 3)
   EIVLTQSPATLSLSPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK;

or (SEQ ID NO: 4)
   EIVLTQSPATLSLSPGERATLSCRASSSVSSSYLYWYQQKPGQAPRLWII

GTSNLASGVPARFSGSGSGTDYTLTISSLEPEDAAVYYCHQYSWSPPTFG

QGTKLEIK.

3. The antibody of aspect 1 or aspect 2, wherein the VH polypeptide comprises an amino acid sequence having at least 80% identity to the amino acid sequence set forth in SEQ ID NO:1.

4. The antibody of any one of aspects 1-3, wherein the VL polypeptide comprises an amino acid sequence having at least 80% identity to the amino acid sequence set forth in SEQ ID NO:2, 3, or 4.

5. The antibody of any one of aspects 1-3, wherein:
   the HCDR1 comprises the amino acid sequence DHTMH (SEQ ID NO:17);
   the HCDR2 comprises the amino acid sequence YFYPRDDSTNYNEKFKG (SEQ ID NO:18);
   the HCDR3 comprises the amino acid sequence GLRYALDY (SEQ ID NO:9);
   the LCDR1 comprises the amino acid sequence RASSSVG/SSSYLY (SEQ ID NO:41);
   the LCDR2 comprises the amino acid sequence G/RT/SS/TN/KLAS (SEQ ID NO:42); and
   the LCDR3 comprises the amino acid sequence HQYA/R/SWSPPT (SEQ ID NO:43), as per Kabat definition;
   or
   the LCDR1 comprises the amino acid sequence RASSSVSSSYLY (SEQ ID NO:10);
   the LCDR2 comprises the amino acid sequence GTSNLAS (SEQ ID NO:11); and
   the LCDR3 comprises the amino acid sequence HQYAWSPPT (SEQ ID NO:12), as per Kabat definition.

6. The antibody of any one of aspects 1-3, wherein:
   the HCDR1 comprises the amino acid sequence DHTMH (SEQ ID NO:17);
   the HCDR2 comprises the amino acid sequence YFYPRDDSTNYNEKFKG (SEQ ID NO:18);
   the HCDR3 comprises the amino acid sequence GLRYALDY (SEQ ID NO:9);
   the LCDR1 comprises the amino acid sequence RASSSVGSSNLY (SEQ ID NO:13);
   the LCDR2 comprises the amino acid sequence RSTKLAS (SEQ ID NO:14); and
   the LCDR3 comprises the amino acid sequence HQYRWSPPT (SEQ ID NO:15), as per Kabat definition.

7. The antibody of any one of aspects 1-3, wherein:
   the HCDR1 comprises the amino acid sequence DHTMH (SEQ ID NO:17);
   the HCDR2 comprises the amino acid sequence YFYPRDDSTNYNEKFKG (SEQ ID NO:18);
   the HCDR3 comprises the amino acid sequence GLRYALDY (SEQ ID NO:9);
   the LCDR1 comprises the amino acid sequence RASSSVSSSYLY (SEQ ID NO:10);
   the LCDR2 comprises the amino acid sequence GTSNLAS (SEQ ID NO:11); and
   the LCDR3 comprises the amino acid sequence HQYSWSPPT (SEQ ID NO:16), as per Kabat definition.

8. The antibody of any one of aspects 1-7, wherein the antibody is a humanized antibody.

9. The antibody of any one of aspects 1-8, wherein the antibody is a chimeric antibody.

10. The antibody of any one of aspects 1-9, wherein the antibody is selected from the group consisting of: an IgG, Fv, single chain antibody, scFv, Fab, F(ab')$_2$, or Fab'.

11. The antibody of any one of aspects 1-10, wherein the antibody is an antibody fragment that binds to MUC1.

12. The antibody of any one of aspects 1-10, wherein the antibody is an IgG.

13. The antibody of any one of aspects 1-10, wherein the antibody is an IgG1.

14. The antibody of any one of aspects 1-10, wherein the antibody is a Fab.

15. The antibody of any one of aspects 1-10, wherein the antibody is a single chain antibody.

16. The antibody of any one of aspects 1-10, wherein the antibody is an scFv.

17. The antibody of any one of aspects 1-16, wherein the antibody is a bispecific antibody comprising a first antigen-binding domain that specifically binds MUC1, and wherein the first antigen binding domain comprises a VH chain and a VL chain as defined in any one of aspects 1 to 7.

18. The antibody of any one of aspects 1-17, wherein the antibody is detectably labeled.

19. The antibody of any one of aspects 1-18, wherein the antibody comprises a covalently linked non-peptide synthetic polymer.

20. The antibody of aspect 19, wherein the synthetic polymer is poly(ethylene glycol) polymer.

21. The antibody of any one of aspects 1-19, wherein the antibody comprises a covalently linked lipid or fatty acid moiety.

22. The antibody of any one of aspects 1-18, wherein the antibody comprises a covalently linked polysaccharide or carbohydrate moiety.

23. The antibody of any one of aspects 1-22, wherein the antibody comprises a contrast agent.

24. The antibody of any one of aspects 1-23, wherein the antibody comprises an affinity domain.

25. The antibody of any one of aspects 1-24, wherein the antibody is immobilized on a solid support.

26. The antibody of any one of aspects 1-25, wherein the antibody comprises a covalently linked cytotoxin.

27. The antibody of any one of aspects 1-26, wherein the antibody comprises a constant region amino acid sequence comprising an amino acid sequence of a sulfatase motif.

28. The antibody of any one of aspects 1-26, wherein the antibody comprises a constant region amino acid sequence comprising an amino acid sequence of a sulfatase motif, and wherein the sulfatase motif is modified to comprise a 2-formylglycine (fGly) moiety.

29. The antibody of aspect 28, wherein the antibody comprises a heterologous moiety covalently linked to the antibody via the fGly moiety.

30. The antibody of aspect 29, wherein the heterologous moiety is selected from a drug, a toxin, a detectable label, a water-soluble polymer, and a synthetic peptide.

31. A nucleic acid encoding a variable heavy (VH) chain, a variable light chain (VL), or both, of the antibody of any one of aspects 1 to 17.

32. The nucleic acid of aspect 31, wherein the antibody is a single chain antibody, and wherein the nucleic acid encodes the single chain antibody.

33. The nucleic acid of aspect 32, wherein the single chain antibody is an scFv.

34. A recombinant expression vector comprising the nucleic acid of any one of aspects 31-33, wherein the nucleic acid is operably linked to a transcriptional control element that is active in a eukaryotic cell.

35. A cell comprising the nucleic acid of any one of aspects 31 to 33 or the expression vector of aspect 34.

36. The cell of aspect 35, wherein the nucleic acid encodes the VH chain of the antibody and the VL polypeptide of the antibody.

37. The cell of aspect 36, wherein the antibody is a single chain antibody, and wherein the nucleic acid encodes the single chain antibody.

38. The cell of aspect 37, wherein the single chain antibody is an scFv.

39. A cell comprising:
a first nucleic acid encoding a variable heavy (VH) chain of the antibody of any one of aspects 1 to 17; and
a second nucleic acid encoding a variable light (VL) chain of the antibody.

40. The cell of aspect 39 comprising:
a first expression vector comprising the first nucleic acid; and
a second expression vector comprising the second nucleic acid.

41. A conjugate, comprising:
the antibody of any one of aspects 1-17; and
an agent conjugated to the antibody.

42. The conjugate of aspect 41, wherein the agent is selected from the group consisting of: a half-life extending moiety, a labeling agent, and a therapeutic agent.

43. A fusion protein, comprising:
a variable heavy (VH) chain, a variable light (VL) chain, or both, of the antibody of any one of aspects 1-17; fused to
a heterologous amino acid sequence.

44. A pharmaceutical composition comprising:
a) the antibody of any one of aspects 1-17; and
b) a pharmaceutically acceptable carrier.

45. A pharmaceutical composition comprising:
a) the conjugate of any one of aspects 41-42; and
b) a pharmaceutically acceptable carrier.

46. A pharmaceutical composition comprising:
a) the fusion protein of aspect 43; and
b) a pharmaceutically acceptable carrier.

47. The pharmaceutical composition of any one of aspects 44-46, further comprising a T cell activator.

48. The pharmaceutical composition of aspect 47, wherein the T cell activator is selected from the group consisting of: an immune checkpoint inhibitor, a cytokine, and an antagonist of an inhibitory immune receptor.

49. The pharmaceutical composition of any one of aspects 44-48, wherein the antibody is encapsulated in a liposome.

50. A method of treating a cell proliferative disorder in a subject, the method comprising: administering to a subject having a cell proliferative disorder a therapeutically effective amount of the pharmaceutical composition of any one of aspects 44-49.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like. Commercially available reagents referred to in the Examples were used according to manufacturer's instructions unless otherwise indicated. The source of cells identified in the Examples and throughout the specification by ECACC accession numbers is the European Collection of Cell Cultures (ECACC), Salisbury, England. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

Example 1: Anti-MUC1 Monoclonal Antibodies

Materials and Methods

SEC HPLC: To determine aggregation, samples were analyzed using analytical size exclusion chromatography (SEC; Tosoh #08541) with a mobile phase of 300 mM NaCl, 25 mM sodium phosphate pH 6.8.

MUC1 ELISA: Antigens were coated directly on a Streptavidin (Pierce, 15500) or Maxisorp (VWR, 62409-024) 96-well plate at 100 ng/well in PBS. Coated plates were incubated at 4° C. overnight. The plates were blocked with casein blocking buffer (Thermo Fisher, 37528) and washed with PBS-Tween-20. Antibodies were serially diluted in PBS, added to the coated wells and incubated for 1h at room temperature with shaking. To test for stickiness, antibodies were also added to uncoated, blocked wells. Peroxidase (HRP)-conjugated anti-Fc secondary (Jackson Immunoresearch, #109-035-098) was used for detection, followed by a TMP substrate (Thermo Fisher, 34028) and H2S04 quench. Absorbance was read at 450 nM on a Molecular Devices plate reader.

Flow cytometric analysis: Cell lines were harvested with Versene, transferred to PBS with 2% FBS (PBS/FBS) and chilled. Cells were incubated for 20-30 minutes on ice with specified Abs (1 µg/test). Following a 1× wash with PBS/FBS, AlexaFluor488 conjugated anti-human IgG-Fc antibody & the dye 7-AAD (used to exclude dead cells) was added and cells were incubated on ice for 20 mins. Samples were washed 2× with PBS/FBS followed by flow cytometric analysis on a FACS Canto™ instrument running FACS-Diva™ software. Analysis was performed by excluding doublets and dead cells and gating on the FSC/SSC cell population. The Geometric Mean Fluorescence Intensity (gMFI) of the AlexaFluor488 channel was determined for each antibody. All samples were run in triplicate. Controls included a MUC1-negative cell line (HCT-116), cells labeled with secondary antibody alone, and unstained cells.

Differential Scanning Fluorimetry. Antibody (10 µL at 1 mg/mL) was used for protein melting temperature measurement using the Protein Thermal Shift Kit (Applied Biosystems). The antibody was mixed with 5 µL of buffer and 2.5 µL of 8× fluorescent dye for a 20 µL reaction. A QuantStudio3 (Applied Biosystems) real-time PCR machine was used to generate a melting curve. The setting was: 25° C. hold for 2 min, followed by 0.05° C./sec. temperature increase to 99° C., followed by a 2 min hold at 99° C. The raw data were analyzed by Protein Thermal Shift software (Applied Biosystems).

Results

Three anti-MUC1 monoclonal antibodies, MUC1 gB06, MUC1 G12, and MUC1 H02 were produced. The three antibodies share the same heavy chain sequence and have different light chain sequences.

The variable heavy chain region sequence with framework regions (underlined) and HCDRs (bold) demarcated based on Chothia definition, Kabat definition, and IMGT definition are shown:

(SEQ ID NO: 1)
EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYCAR

GLRYALDYWGQGTLVTVSS (Chothia definition)

(SEQ ID NO: 1)
EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYCAR

GLRYALDYWGQGTLVTVSS (Kabat definition)

(SEQ ID NO: 1)
EVQLVQSGAEVKKPGATVKISCKVSGYTFTDHTMHWIKQRPGKGLEWM

GYFYPRDDSTNYNEKFKGRVTLTADKSTDTAYMELSSLRSEDTAVYYC

ARGLRYALDYWGQGTLVTVSS (IMGT definition)

The variable light chain region sequence with framework regions (underlined) and LCDRs (bold) demarcated based on Chothia definition, Kabat definition, and IMGT definition are shown:

gB06, VL:
(SEQ ID NO: 2)
EIVLTQSPATLSLSPGERATLSCRASSSVSSSYLYWYQQKPGQAPRLWIY

GTSNLASGVPARFSGSGSGTDYTLTISSLEPEDAAVYYCHQYAWSPPT

FGQGTKLEIK (Chothia and Kabat definition)

G12, VL:
(SEQ ID NO: 3)
EIVLTQSPATLSLSPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK (Chothia and Kabat definition)

H02, VL:
(SEQ ID NO: 4)
EIVLTQSPATLSLSPGERATLSCRASSSVSSSYLYWYQQKPGQAPRLWII

GTSNLASGVPARFSGSGSGTDYTLTISSLEPEDAAVYYCHQYSWSPPTFG

QGTKLEIK (Chothia and Kabat definition)

gB06, VL:
(SEQ ID NO: 2)
EIVLTQSPATLSLSPGERATLSCRASSSVSSSYLYWYQQKPGQAPRLWI

YGTSNLASGVPARFSGSGSGTDYTLTISSLEPEDAAVYYCHQYAWSPPTF

GQGTKLEIK (IMGT definition)

-continued

G12, VL:
(SEQ ID NO: 3)
EIVLTQSPATLSLSPGERATLSCRASSSVGSSNLYWYQQKPGQAPRLWIY

RSTKLASGVPARFSGSGSGTDYTLTISSLEPEDAAVYYCHQYRWSPPTFG

QGTKLEIK (IMGT definition)

H02, VL:
(SEQ ID NO: 4)
EIVLTQSPATLSLSPGERATLSCRASSSVSSSYLYWYQQKPGQAPRLWII

GTSNLASGVPARFSGSGSGTDYTLTISSLEPEDAAVYYCHQYSWSPPTFG

QGTKLEIK (IMGT definition)

FIG. 1 shows that anti-MUC1 monoclonal antibodies, MUC1 gB06, MUC1 G12, and MUC1 H02 are more than 99%, more than 99%, and more than 98% monomeric, respectively, as determined by size exclusion chromatography (SEC).

Figure 2B:
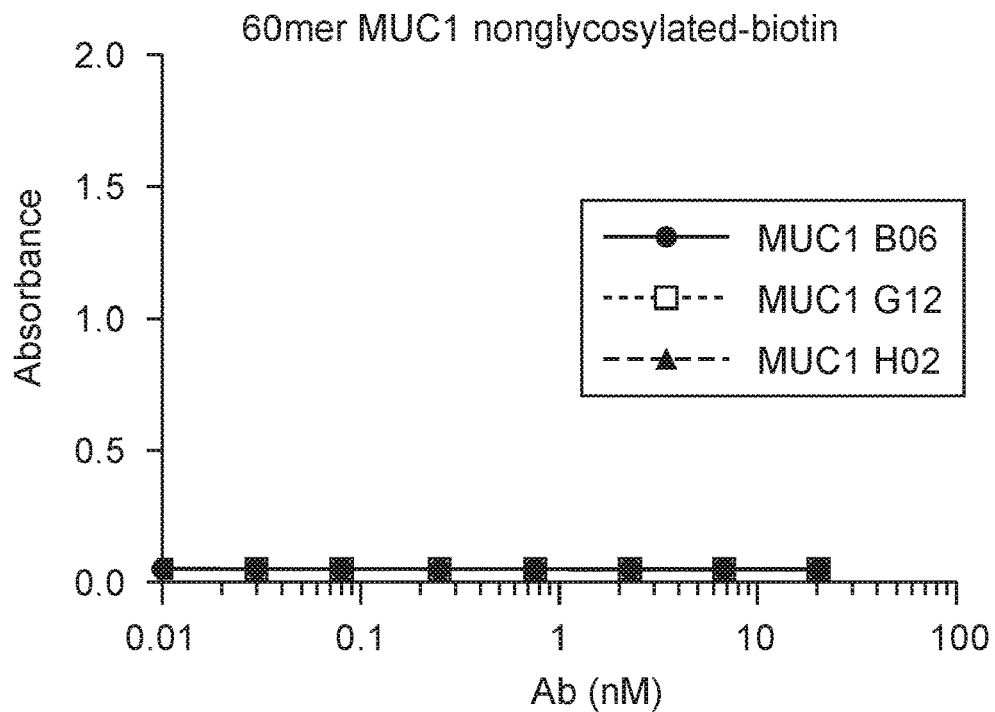
Figure 2C:
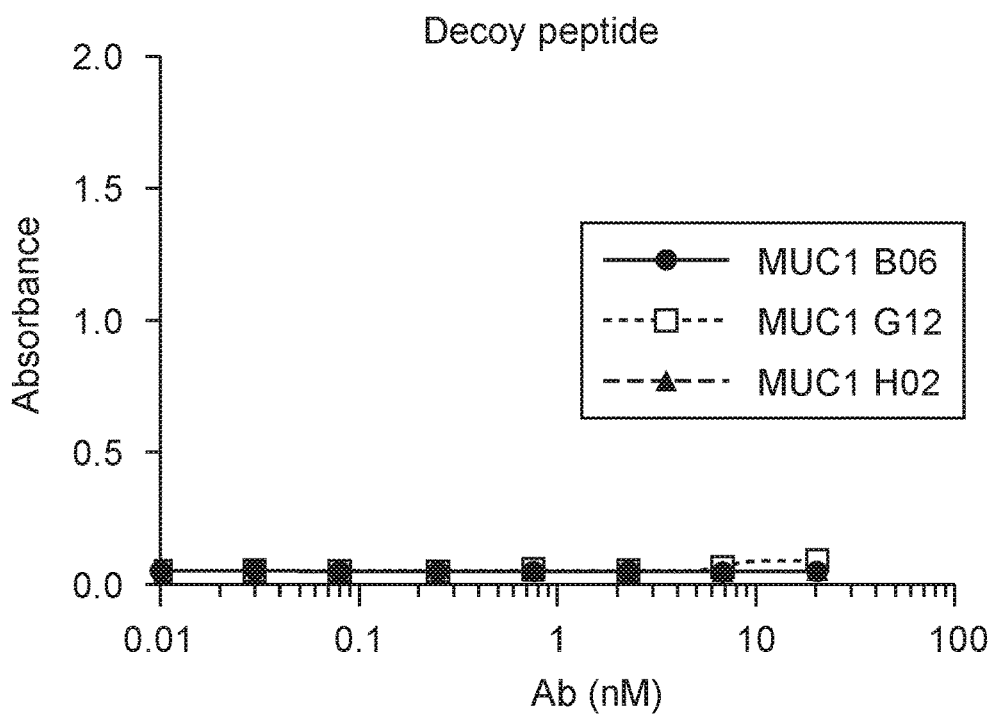

FIGS. 2A-2C show that anti-MUC1 monoclonal antibodies, MUC1 gB06, MUC1 G12, and MUC1 H02 bind to recombinant 20mer MUC1 glycosylated-biotin but not to recombinant 60mer MUC1 non-glycosylated-biotin or to a decoy peptide as assessed by ELISA. 20mer MUC1 glycosylated-biotin refers to a peptide comprising the sequence VTSAPDTRPAPGSTAPPAHG (SEQ ID NO:26) with Tn (GalNac) antigen or sialyl Tn (Neu5Aca2-6GalNAc) antigen modifications on some of the S/T residues, where biotin in conjugated to the N-terminus. 60mer MUC1 non-glycosylated-biotin refers to a peptide comprising the sequence VTSAPDTRPAPGSTAPPAHGVTSAPDTRPAPGSTAP-PAHGVTSAPDTRPAPGSTAPPAHG (SEQ ID NO:27), where biotin in conjugated to the N-terminus. Decoy peptide refers to a peptide comprising the sequence PLPVTSTS-SASTGHATPLAV (SEQ ID NO:28), with Tn (GalNac) antigen or sialyl Tn (Neu5Aca2-6GalNAc) antigen modifications on some of the S/T residues.

Figure 3A:
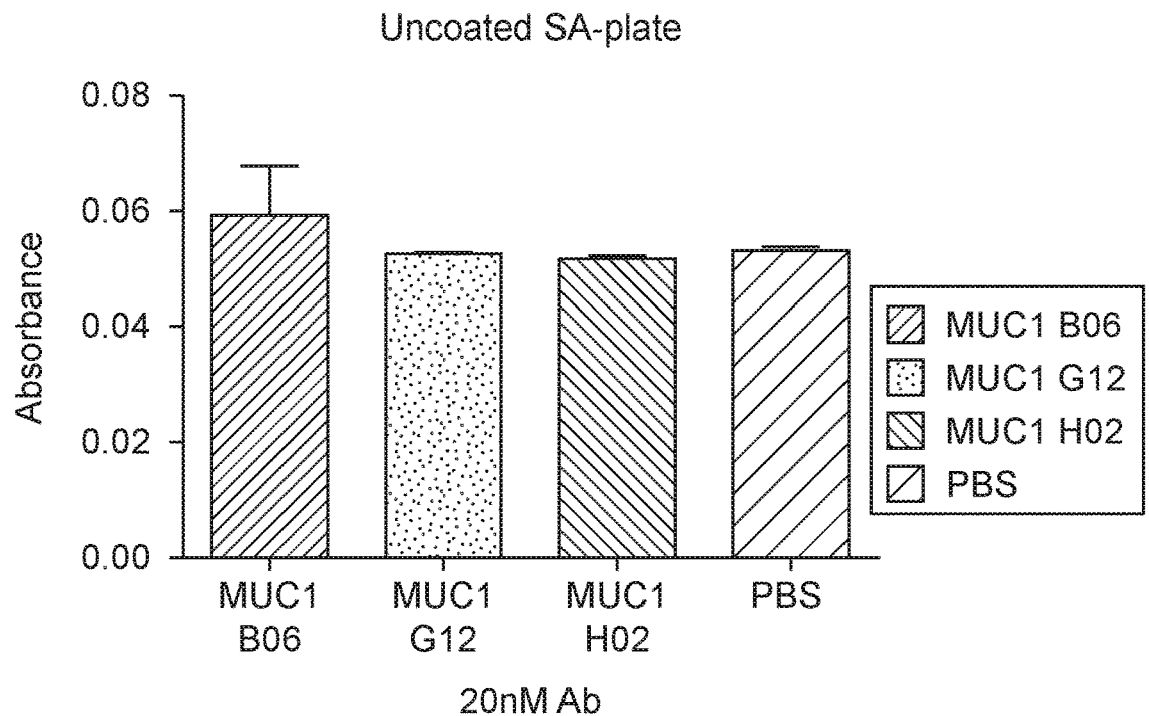
FIGS. 3A-3B show level of binding by the anti-MUC1 antibodies, MUC1 gB06, MUC1 G12, and MUC1 H02 to uncoated streptavidin or Maxisorp plate.
Figure 3B:
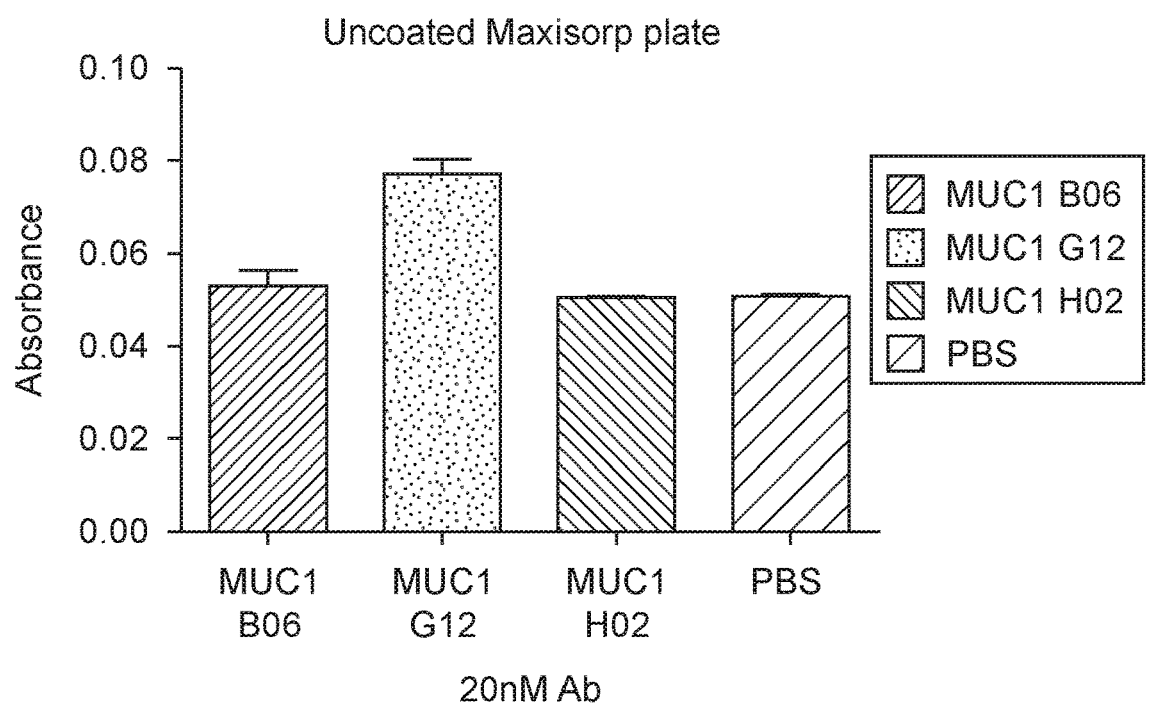

FIGS. 3A-3B show level of binding by the anti-MUC1 antibodies, MUC1 gB06, MUC1 G12, and MUC1 H02 to uncoated streptavidin or Maxisorp plate.

Figure 4:
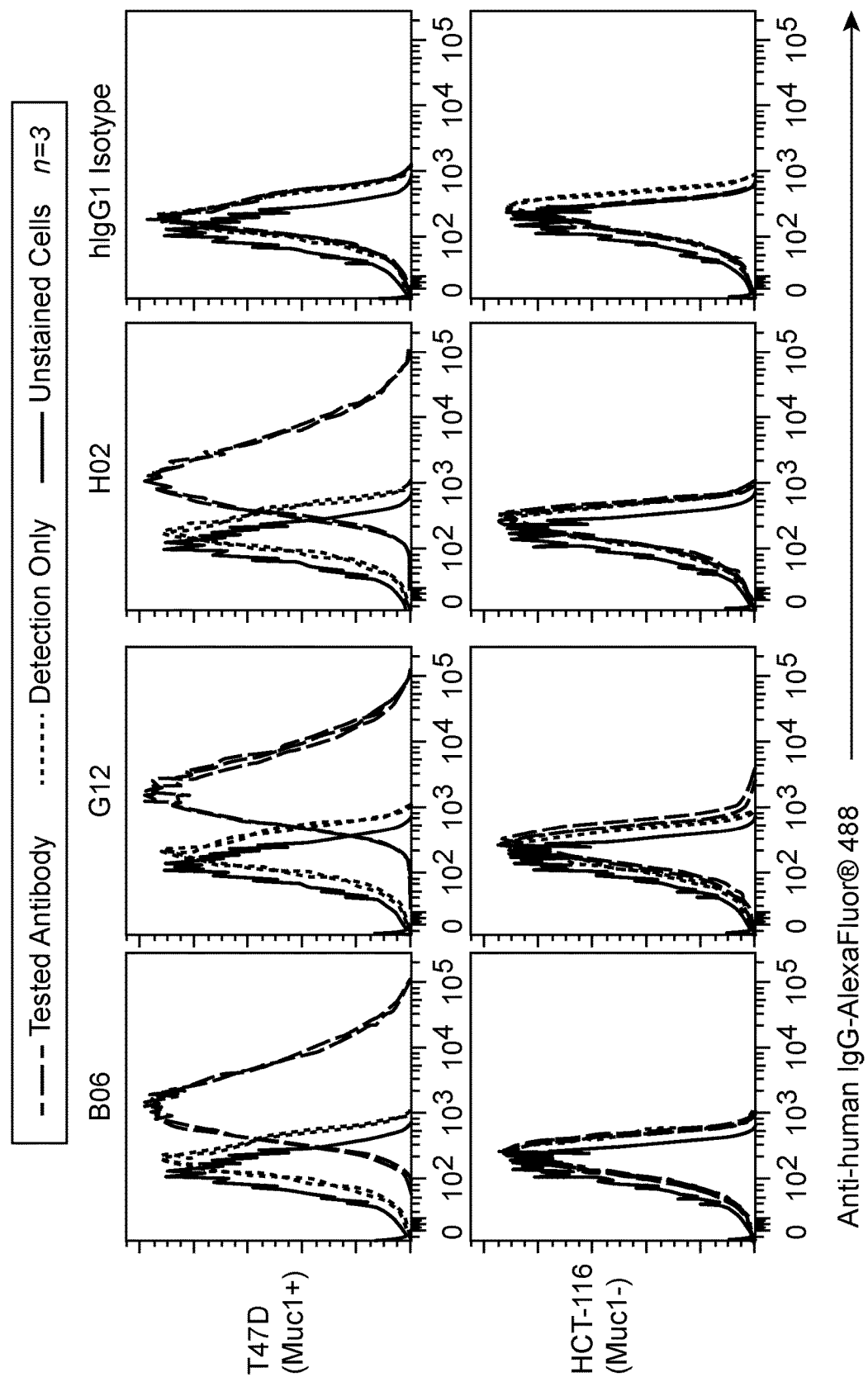
FIG. 4 shows superimposed histograms showing the binding of the indicated antibodies to the named cell lines, tested in triplicates.

FIG. 4 shows superimposed histograms showing the binding of the indicated antibodies to the named cell lines, tested in triplicates.

Figure 5:
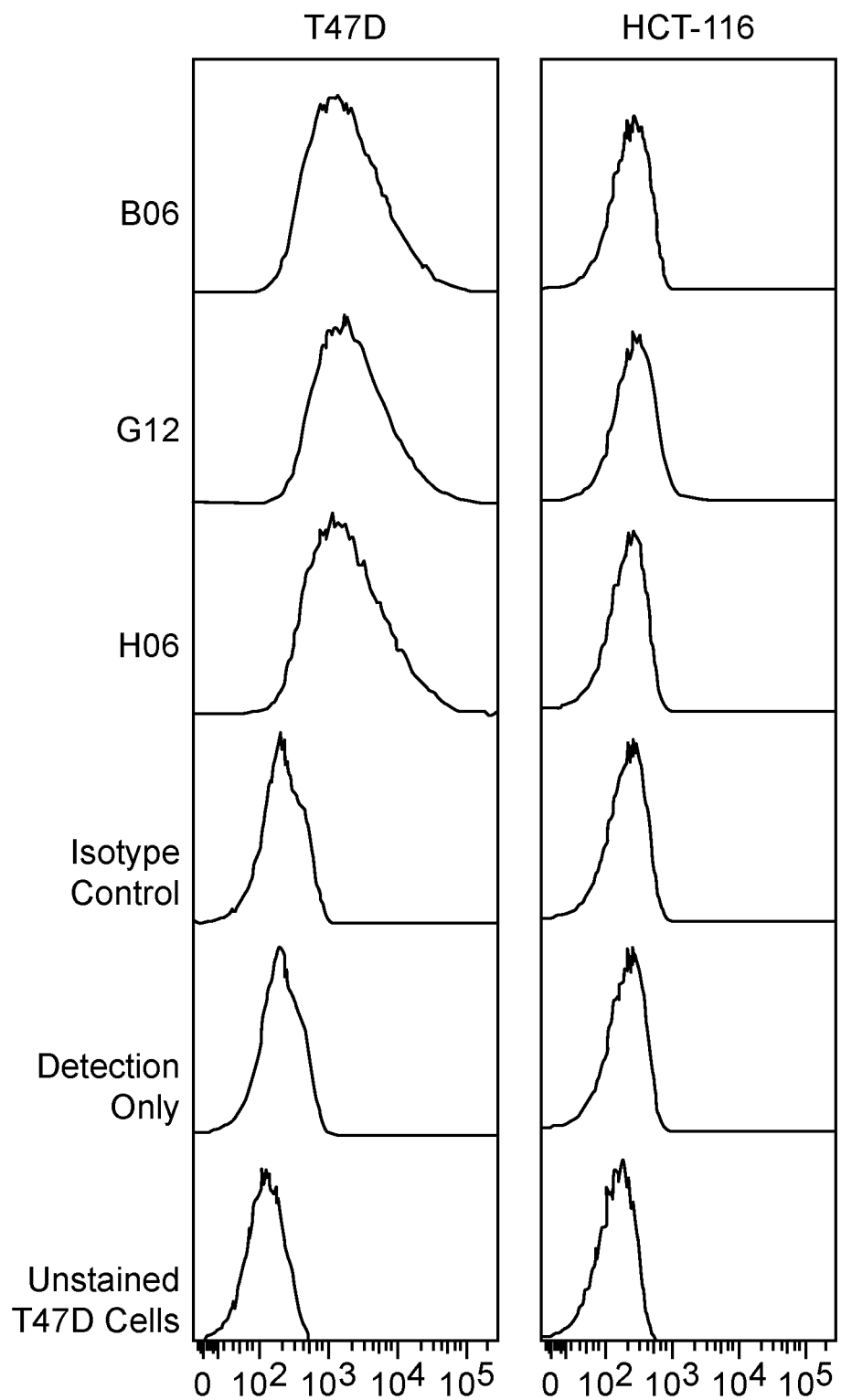
FIG. 5 shows staggered histograms showing the binding of the indicated antibodies to the named cell lines.

FIG. 5 shows staggered histograms showing the binding of the indicated antibodies to the named cell lines.

Figure 6:
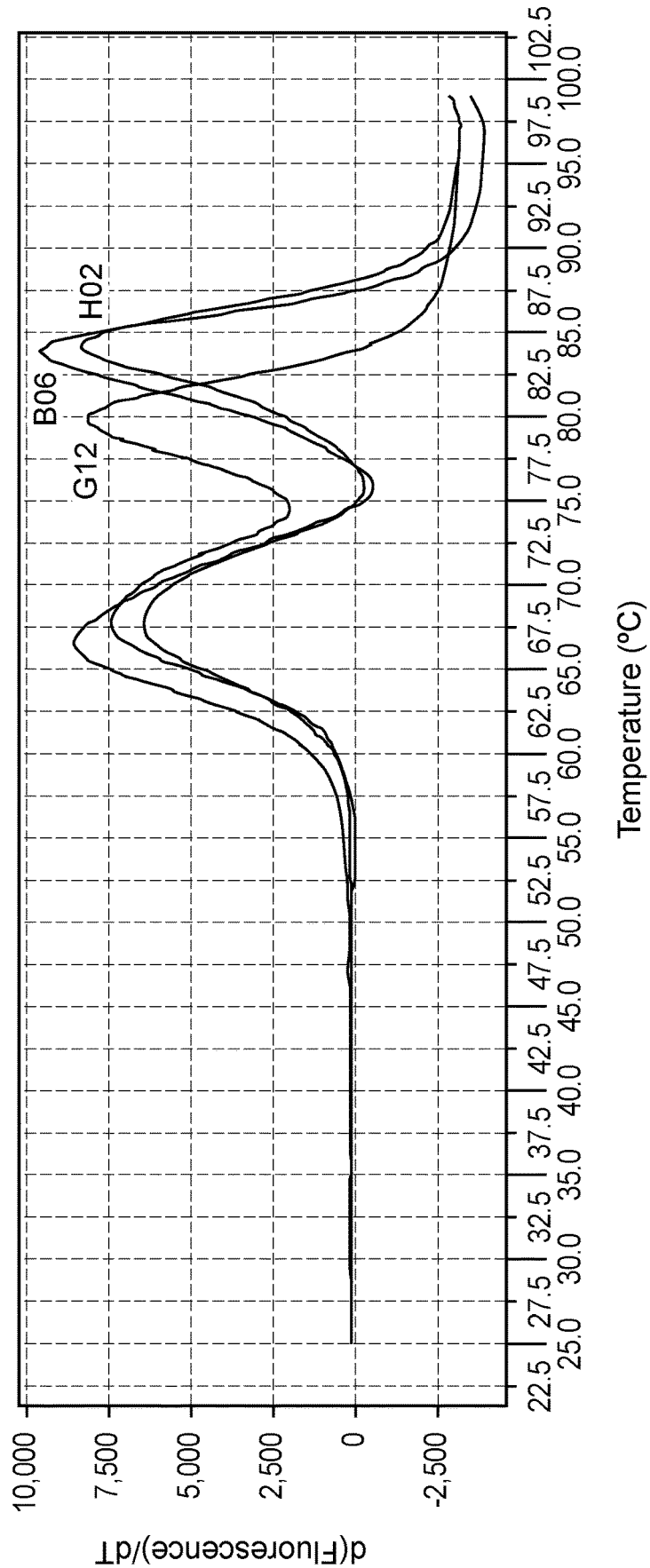
FIG. 6 shows the melting temperature of CH2 and Fab regions of the B06, G12, and H02 anti-MUC1 antibodies as determined by differential scanning fluorimetry.

FIG. 6 shows the melting temperature of CH2 and Fab regions of the B06, G12, and H02 anti-MUC1 antibodies as determined by differential scanning fluorimetry.

Example 2: In Vivo Efficacy of Anti-Muc1 Monoclonal Antibody

Xenograft Studies

Methods: Female NCG mice (10/group) were implanted with estrogen pellets (0.36 mg/90 days, 17β-estradiol), and then were inoculated subcutaneously with 20 million T47D cells in PBS with Matrigel (1:1 vol/vol). On the day before treatment began (Day 0), all animals received an intravenous dose of 10 mg/kg human IgG.

Treatment began when the tumors reached an average of 223 mm³ (Day 1). For treatment, animals were dosed intravenously with vehicle alone or with B06 antibody. Treatment dosing occurred weekly for 4 total doses. The animals were monitored twice weekly for body weight and tumor size. Animals were euthanized when tumors reached 2000 mm³.

Results: Tumors in the vehicle control group grew slowly but consistently throughout the study. Animals dosed with 10 mg/kg of B06 antibody led to tumor stasis.

Figure 7:
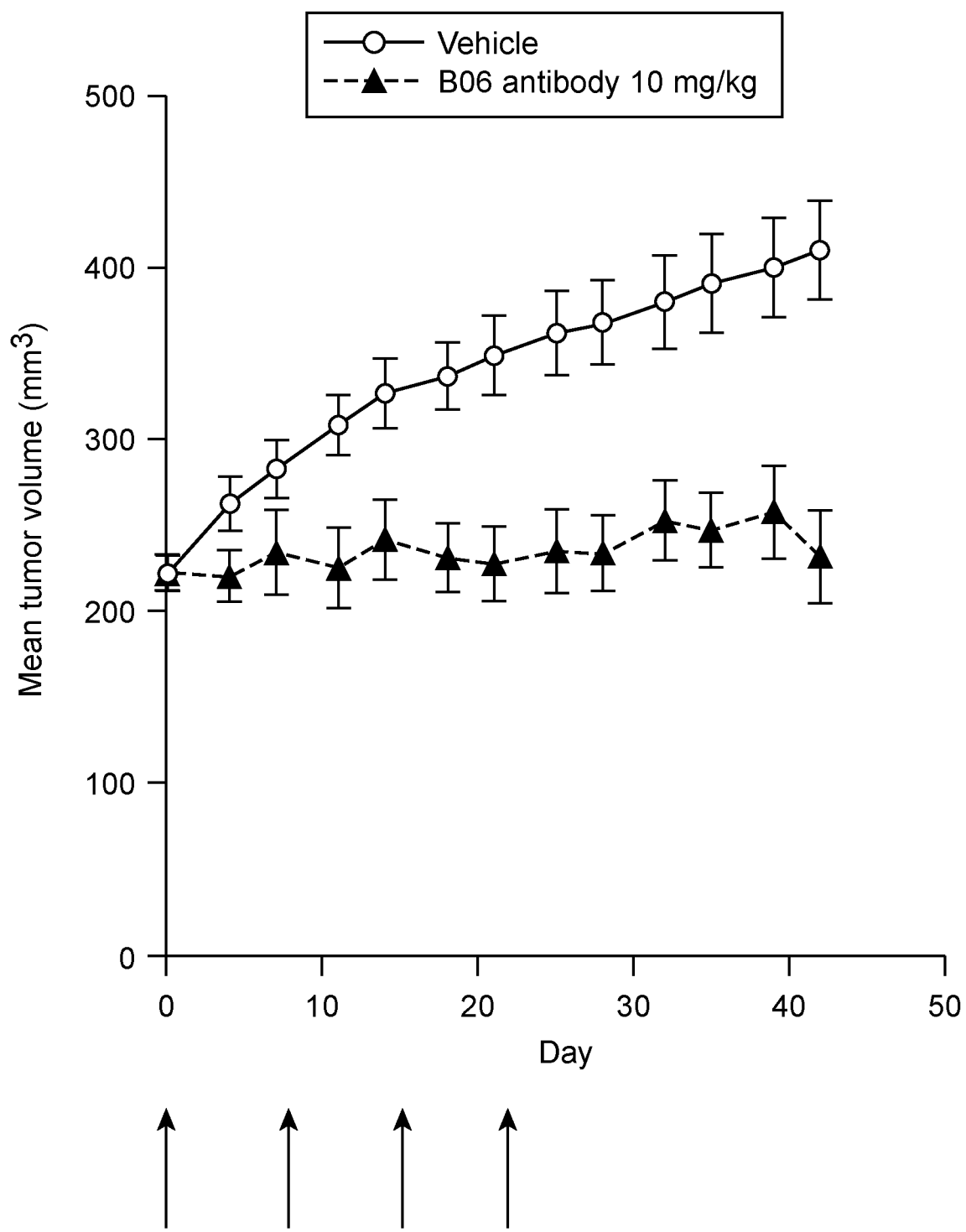
FIG. 7 shows in vivo efficacy of anti-MUC1 antibody B06 against a T47D xenograft. n=10 mice/group; arrows indicates days on which the antibody or vehicle was administered.

FIG. 7 shows in vivo efficacy of anti-MUC1 antibody B06 against a T47D xenograft. n=10 mice/group; arrows indicates days on which the antibody or vehicle was administered.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An antibody or fragment thereof that specifically binds to Mucin-1 (MUC-1), wherein the antibody or fragment thereof comprises:
    a heavy chain complementarity determining region 1 (HCDR1), a heavy chain complementarity determining region 2 (HCDR2), and a heavy chain complementarity determining region 3 (HCDR3) as set forth in a variable heavy (VH) chain comprising the amino acid sequence of SEQ ID NO: 1; and
    a light chain complementarity determining region 1 (LCDR1), a light chain complementarity determining region 2 (LCDR2), and a light chain complementarity determining region 3 (LCDR3) as set forth in a variable light (VL) chain comprising the amino acid sequence of any one of SEQ ID NOs: 2, 3, or 4.

2. The antibody or fragment thereof according to claim 1, comprising:
    a VH chain comprising:
        an HCDR1 comprising the amino acid sequence DHTMEI (SEQ ID NO: 17);
        an HCDR2 comprising the amino acid sequence YFYPRDDSTNYNEKFKG (SEQ ID NO: 18); and
        an HCDR3 comprising the amino acid sequence GLRYALDY (SEQ ID NO: 9); and
    a VL chain comprising:
        a) an LCDR1 comprising the amino acid sequence RASSSVSSSYLY (SEQ ID NO: 10),
            an LCDR2 comprising the amino acid sequence GTSNLAS (SEQ ID NO: 11), and
            an LCDR3 comprising the amino acid sequence HQYAWSPPT (SEQ ID NO: 12); or
        b) an LCDR1 comprising the amino acid sequence RASSSVGSSNLY (SEQ ID NO: 13),
            an LCDR2 comprising the amino acid sequence RSTKLAS (SEQ ID NO: 14), and
            an LCDR3 comprising the amino acid sequence HQYRWSPPT (SEQ ID NO: 15; or
        c) an LCDR1 comprising the amino acid sequence RASSSVSSSYLY (SEQ ID NO: 10),
            an LCDR2 comprising the amino acid sequence GTSNLAS (SEQ ID NO: 11), and
            an LCDR3 comprising the amino acid sequence HQYSWSPPT (SEQ ID NO: 16).

3. The antibody or fragment thereof according to claim 1, wherein the VH chain comprises an amino acid sequence having at least 80% identity to the amino acid sequence set forth in SEQ ID NO: 1.

4. The antibody or fragment thereof according to claim 3, wherein the VL chain comprises an amino acid sequence having at least 80% identity to the amino acid sequence set forth in any one of SEQ ID NO: 2, 3, or 4.

5. The antibody or fragment thereof according to claim 1, comprising:
    (i) an HCDR1 comprising the amino acid sequence DHTMH (SEQ ID NO: 17),
        an HCDR2 comprising the amino acid sequence YFYPRDDSTNYNEKFKG (SEQ ID NO: 18),
        an HCDR3 comprising the amino acid sequence GLRYALDY (SEQ ID NO: 9),
        an LCDR1 comprising the amino acid sequence RASSSVSSSYLY (SEQ ID NO: 10),
        an LCDR2 comprising the amino acid sequence GTSNLAS (SEQ ID NO: 11), and
        an LCDR3 comprising the amino acid sequence HQYAWSPPT (SEQ ID NO: 12),
    as per Kabat definition; or
    (ii) an HCDR1 comprising the amino acid sequence GYTFTDH (SEQ ID NO: 7),
        an HCDR2 comprising the amino acid sequence YPRDDS (SEQ ID NO: 8),
        an HCDR3 comprising the amino acid sequence GLRYALDY (SEQ ID NO: 9),
        an LCDR1 comprising the amino acid sequence RASSSVSSSYLY (SEQ ID NO: 10),
        an LCDR2 comprising the amino acid sequence GTSNLAS (SEQ ID NO: 11), and
        an LCDR3 comprising the amino acid sequence HQYAWSPPT (SEQ ID NO: 12), as per Chothia definition; or
    (iii) an HCDR1 comprising the amino acid sequence GYTFTDHT (SEQ ID NO: 34),
        an HCDR2 comprising the amino acid sequence FYPRDDST (SEQ ID NO: 44), an HCDR3 comprising the amino acid sequence ARGLRYALDY (SEQ ID NO: 45),
an LCDR1 comprising the amino acid sequence SSVSSSY (SEQ ID NO: 33),
an LCDR2 comprising the amino acid sequence GT, and
an LCDR3 comprising the amino acid sequence HQYAWSPPT (SEQ ID NO: 12), as per IMGT definition.

6. The antibody or fragment thereof according to claim 1, comprising:
(i) an HCDR1 comprising the amino acid sequence DHTMH (SEQ ID NO: 17),
an HCDR2 comprising the amino acid sequence YFYPRDDSTNYNEKFKG (SEQ ID NO: 18),
an HCDR3 comprising the amino acid sequence GLRYALDY (SEQ ID NO: 9),
an LCDR1 comprising the amino acid sequence RASSSVGSSNLY (SEQ ID NO: 13),
an LCDR2 comprising the amino acid sequence RSTKLAS (SEQ ID NO: 14), and
an LCDR3 comprising the amino acid sequence HQYRWSPPT (SEQ ID NO: 15),
as per Kabat definition, or
(ii) an HCDR1 comprising the amino acid sequence GYTFTDH (SEQ ID NO: 7),
an HCDR2 comprising the amino acid sequence YPRDDS (SEQ ID NO: 8),
an HCDR3 comprising the amino acid sequence GLRYALDY (SEQ ID NO: 9),
an LCDR1 comprising the amino acid sequence RASSSVGSSNLY (SEQ ID NO: 13),
an LCDR2 comprising the amino acid sequence RSTKLAS (SEQ ID NO: 14), and
an LCDR3 comprising the amino acid sequence HQYRWSPPT (SEQ ID NO: 15), as per Chothia definition; or
(iii) an HCDR1 comprising the amino acid sequence GYTFTDHT (SEQ ID NO: 34),
an HCDR2 comprising the amino acid sequence FYPRDDST (SEQ ID NO: 44),
an HCDR3 comprising the amino acid sequence ARGLRYALDY (SEQ ID NO: 45),
an LCDR1 comprising the amino acid sequence SSVGSSN (SEQ ID NO: 46),
an LCDR2 comprising the amino acid sequence RS, and
an LCDR3 comprising the amino acid sequence HQYRWSPPT (SEQ ID NO: 15), as per IMGT definition.

7. The antibody or fragment thereof according to claim 1, comprising:
(i) an HCDR1 comprising the amino acid sequence DHTMH (SEQ ID NO: 17),
an HCDR2 comprising the amino acid sequence YFYPRDDSTNYNEKFKG (SEQ ID NO: 18);
an HCDR3 comprising the amino acid sequence GLRYALDY (SEQ ID NO: 9),
an LCDR1 comprising the amino acid sequence RASSSVSSSYLY (SEQ ID NO: 10),
an LCDR2 comprising the amino acid sequence GTSNLAS (SEQ ID NO: 11), and
an LCDR3 comprising the amino acid sequence HQYSWSPPT (SEQ ID NO: 16),
as per Kabat definition or
(ii) an HCDR1 comprising the amino acid sequence GYTFTDH (SEQ ID NO: 7),
an HCDR2 comprising the amino acid sequence YPRDDS (SEQ ID NO: 8),
an HCDR3 comprising the amino acid sequence GLRYALDY (SEQ ID NO: 9),
an LCDR1 comprising the amino acid sequence RASSSVSSSYLY (SEQ ID NO: 10),
an LCDR2 comprising the amino acid sequence GTSNLAS (SEQ ID NO: 11), and
an LCDR3 comprising the amino acid sequence HQYSWSPPT (SEQ ID NO: 16), as per Chothia definition; or
(iii) an HCDR1 comprising the amino acid sequence GYTFTDHT (SEQ ID NO: 34),
an HCDR2 comprising the amino acid sequence FYPRDDST (SEQ ID NO: 44),
an HCDR3 comprising the amino acid sequence ARGLRYALDY (SEQ ID NO: 45),
an LCDR1 comprising the amino acid sequence SSVSSSY (SEQ ID NO: 33),
an LCDR2 comprising the amino acid sequence GT, and
an LCDR3 comprising the amino acid sequence HQYSWSPPT (SEQ ID NO: 16), as per IMGT definition.

8. The antibody or fragment thereof according to claim 1, wherein the antibody is a humanized antibody or a chimeric antibody.

9. The antibody or fragment thereof according to claim 1, wherein the antibody or fragment thereof is selected from the group consisting of: an IgG, Fv, single chain antibody, scFv, Fab, F(ab')2, or Fab'.

10. The antibody or fragment thereof according to claim 9, wherein the antibody is an IgG1 or a bispecific antibody.

11. The antibody or fragment thereof according to claim 1, wherein the antibody or fragment thereof is detectably labeled.

12. The antibody or fragment thereof according to claim 1, wherein the antibody or fragment thereof comprises a covalently linked lipid or fatty acid moiety.

13. The antibody or fragment thereof according to claim 1, wherein the antibody or fragment thereof is linked to a contrast agent.

14. The antibody or fragment thereof according to claim 1, wherein the antibody or fragment thereof is immobilized on a solid support.

15. The antibody or fragment thereof according to claim 1, wherein the antibody or fragment thereof comprises a constant region comprising an amino acid sequence of a sulfatase motif.

16. The antibody or fragment thereof according to claim 1, wherein the antibody or fragment thereof comprises a constant region comprising an amino acid sequence of a sulfatase motif, and wherein the sulfatase motif is modified to comprise a 2-formylglycine (fGly) moiety.

17. A pharmaceutical composition comprising:
a. the antibody or fragment thereof according to claim 1; and
b. a pharmaceutically acceptable carrier.

18. The pharmaceutical composition of claim 17, further comprising a T cell activator.

19. The pharmaceutical composition of claim 18, wherein the T cell activator is selected from the group consisting of: an immune checkpoint inhibitor, a cytokine, and an antagonist of an inhibitory immune receptor.

20. The pharmaceutical composition of claim 17, wherein the antibody or fragment thereof is encapsulated in a liposome.

21. The antibody or fragment thereof according to claim 1, wherein the VH chain comprises the amino acid sequence as set forth in SEQ ID NO: 1, and wherein the VL chain comprises the amino acid sequence as set forth in any one of SEQ ID NO: 2, SEQ ID NO: 3, or SEQ ID NO: 4.

22. The antibody or fragment thereof according to claim 21, wherein the antibody or fragment thereof comprises a constant region comprising an amino acid sequence of a sulfatase motif.

23. The antibody or fragment thereof according to claim 22, wherein the sulfatase motif is modified to comprise a 2-formylglycine (fGly) moiety.

* * * * *